US008303630B2

(12) United States Patent
Abdou

(10) Patent No.: US 8,303,630 B2
(45) Date of Patent: Nov. 6, 2012

(54) DEVICES AND METHODS FOR THE MINIMALLY INVASIVE TREATMENT OF SPINAL STENOSIS

(76) Inventor: Samy Abdou, San Diego, CA (US)

(*) Notice: Subject to any disclaimer, the term of this patent is extended or adjusted under 35 U.S.C. 154(b) by 451 days.

(21) Appl. No.: 11/881,584

(22) Filed: Jul. 27, 2007

(65) Prior Publication Data

US 2008/0027438 A1 Jan. 31, 2008

Related U.S. Application Data

(60) Provisional application No. 60/834,209, filed on Jul. 27, 2006, provisional application No. 60/834,003, filed on Jul. 28, 2006, provisional application No. 60/860,942, filed on Nov. 24, 2006.

(51) Int. Cl.
*A61B 17/70* (2006.01)

(52) U.S. Cl. ......... 606/249; 606/86 A; 606/99; 606/105; 606/279

(58) Field of Classification Search ............... 606/86 A, 606/90, 99, 105, 248, 249
See application file for complete search history.

(56) References Cited

U.S. PATENT DOCUMENTS

| | | | |
|---|---|---|---|
| 2,248,054 A | 7/1941 | Becker |
| 2,774,350 A | 12/1956 | Cleveland |
| 3,090,386 A | 5/1963 | Babcock |
| 3,659,595 A | 5/1972 | Haboush |
| 3,865,105 A | 2/1975 | Lode |
| 4,037,592 A | 7/1977 | Kronner |
| 4,289,123 A | 9/1981 | Dunn |
| 4,569,662 A | 2/1986 | Dragan |
| 4,580,563 A | 4/1986 | Gross |
| 4,722,331 A | 2/1988 | Fox |
| 4,790,303 A | 12/1988 | Steffee |
| 4,899,761 A | 2/1990 | Brown et al. |
| 4,903,692 A | 2/1990 | Reese |
| 5,133,717 A | 7/1992 | Chopin |
| 5,254,118 A | 10/1993 | Mirkovic |
| 5,275,601 A | 1/1994 | Gogolewski et al. |
| 5,330,468 A | 7/1994 | Burkhart |
| 5,334,205 A | 8/1994 | Cain |
| 5,354,292 A | 10/1994 | Braeuer et al. |
| 5,360,429 A | 11/1994 | Jeanson et al. |
| 5,413,576 A | 5/1995 | Rivard |

(Continued)

FOREIGN PATENT DOCUMENTS

DE   10035182   2/2002

(Continued)

OTHER PUBLICATIONS

Derwent English Language Abstract WPI Acct. No. 2002-155861-200221 for German Patent No. DE10035182 (Item CU).

(Continued)

*Primary Examiner* — Eduardo C Robert
*Assistant Examiner* — Jerry Cumberledge
(74) *Attorney, Agent, or Firm* — Gazdzinski & Associates, PC

(57) ABSTRACT

Multiple implants and methods for the minimally invasive treatment of spinal stenosis are disclosed. A spinal implant device includes a spacer region and an attachment region. The spacer region is adapted to be positioned between first and second spinous processes of first and second vertebral bodies to limit movement of the first spinous process and the second spinous process toward one another. The attachment region attaches to the first spinous process via a fastener that extends substantially along a long axis of the spinous process.

29 Claims, 31 Drawing Sheets

U.S. PATENT DOCUMENTS

| | | |
|---|---|---|
| 5,456,714 A | 10/1995 | Owen |
| 5,484,437 A | 1/1996 | Michelson |
| 5,484,440 A | 1/1996 | Allard |
| 5,531,747 A | 7/1996 | Ray |
| 5,545,164 A | 8/1996 | Howland |
| 5,558,674 A | 9/1996 | Heggeness et al. |
| 5,569,248 A | 10/1996 | Mathews |
| 5,609,634 A | 3/1997 | Voydeville |
| 5,616,142 A | 4/1997 | Yuan et al. |
| 5,645,599 A | 7/1997 | Samani |
| 5,672,175 A | 9/1997 | Martin |
| 5,672,176 A | 9/1997 | Biedermann et al. |
| 5,681,312 A | 10/1997 | Yuan et al. |
| 5,928,139 A | 7/1999 | Koros et al. |
| 5,928,233 A | 7/1999 | Apfelbaum et al. |
| 5,971,987 A | 10/1999 | Huxel et al. |
| 5,976,146 A * | 11/1999 | Ogawa et al. ............... 606/86 R |
| 5,993,449 A | 11/1999 | Schlapfer et al. |
| 6,039,761 A | 3/2000 | Li et al. |
| 6,059,786 A | 5/2000 | Jackson |
| 6,086,589 A | 7/2000 | Kuslich |
| 6,090,113 A | 7/2000 | Le Couedic et al. |
| 6,117,135 A | 9/2000 | Schlapfer et al. |
| 6,123,707 A | 9/2000 | Wagner |
| 6,139,549 A | 10/2000 | Keller |
| 6,159,244 A | 12/2000 | Suddaby |
| 6,193,757 B1 | 2/2001 | Foley et al. |
| 6,226,548 B1 | 5/2001 | Foley |
| 6,306,136 B1 | 10/2001 | Baccelli |
| 6,309,391 B1 | 10/2001 | Crandall et al. |
| 6,312,431 B1 | 11/2001 | Asfora |
| 6,319,002 B1 | 11/2001 | Pond |
| 6,319,257 B1 | 11/2001 | Carignan |
| 6,331,179 B1 | 12/2001 | Freid et al. |
| 6,355,038 B1 | 3/2002 | Pisharodi |
| 6,402,750 B1 | 6/2002 | Atkinson et al. |
| 6,402,752 B2 | 6/2002 | Schaffler-Wachter et al. |
| 6,419,676 B1 | 7/2002 | Zucherman et al. |
| 6,419,677 B2 | 7/2002 | Zucherman et al. |
| 6,428,576 B1 | 8/2002 | Haldimann |
| 6,432,140 B1 | 8/2002 | Lin |
| 6,440,133 B1 | 8/2002 | Beale |
| 6,451,019 B1 | 9/2002 | Zucherman et al. |
| 6,451,020 B1 | 9/2002 | Zucherman et al. |
| 6,478,800 B1 * | 11/2002 | Fraser et al. ..................... 606/99 |
| 6,508,839 B1 | 1/2003 | Lambrecht et al. |
| 6,524,315 B1 | 2/2003 | Selvitelli et al. |
| 6,530,929 B1 | 3/2003 | Justis et al. |
| 6,547,790 B2 | 4/2003 | Harkey, III et al. |
| 6,558,386 B1 | 5/2003 | Cragg |
| 6,558,390 B2 | 5/2003 | Cragg |
| 6,599,294 B2 * | 7/2003 | Fuss et al. ....................... 606/99 |
| 6,599,295 B1 | 7/2003 | Tornier et al. |
| 6,645,207 B2 | 11/2003 | Dixon et al. |
| 6,663,631 B2 | 12/2003 | Kuntz |
| 6,665,555 B2 | 12/2003 | Henderson et al. |
| 6,695,842 B2 | 2/2004 | Zucherman et al. |
| 6,716,212 B1 | 4/2004 | Pickens |
| 6,719,795 B1 | 4/2004 | Cornwall et al. |
| 6,730,126 B2 | 5/2004 | Boehm, Jr. et al. |
| 6,733,534 B2 | 5/2004 | Sherman |
| 6,739,068 B1 | 5/2004 | Rinner |
| 6,740,087 B2 | 5/2004 | Knox |
| 6,740,090 B1 | 5/2004 | Cragg et al. |
| 6,746,449 B2 | 6/2004 | Jones et al. |
| 6,749,614 B2 | 6/2004 | Teitelbaum et al. |
| 6,755,841 B2 | 6/2004 | Fraser et al. |
| 6,761,720 B1 | 7/2004 | Senegas |
| 6,783,547 B2 | 8/2004 | Castro |
| 6,790,210 B1 | 9/2004 | Cragg et al. |
| 6,805,697 B1 | 10/2004 | Helm et al. |
| 6,821,277 B2 | 11/2004 | Teitelbaum |
| 6,830,571 B2 | 12/2004 | Lenke et al. |
| 6,875,211 B2 | 4/2005 | Nichols et al. |
| 6,884,243 B2 | 4/2005 | Sellers |
| 6,899,716 B2 | 5/2005 | Cragg |
| 6,921,403 B2 | 7/2005 | Cragg et al. |
| 6,945,975 B2 | 9/2005 | Dalton et al. |
| 7,008,422 B2 | 3/2006 | Foley et al. |
| 7,011,658 B2 | 3/2006 | Young |
| 7,011,660 B2 * | 3/2006 | Sherman et al. ............ 606/86 A |
| 7,014,633 B2 | 3/2006 | Cragg |
| 7,060,066 B2 | 6/2006 | Zhao et al. |
| 7,087,058 B2 | 8/2006 | Cragg |
| 7,118,579 B2 | 10/2006 | Michelson |
| 7,118,580 B1 * | 10/2006 | Beyersdorff et al. ............ 606/99 |
| 7,153,281 B2 | 12/2006 | Homes |
| 7,160,300 B2 | 1/2007 | Jackson |
| 7,232,463 B2 | 6/2007 | Falahee |
| 7,338,527 B2 * | 3/2008 | Blatt et al. .................. 623/17.15 |
| 7,455,685 B2 | 11/2008 | Justis |
| 7,572,276 B2 | 8/2009 | Lim et al. |
| 7,585,316 B2 | 9/2009 | Trieu |
| 2001/0012938 A1 | 8/2001 | Zucherman |
| 2001/0031965 A1 * | 10/2001 | Zucherman et al. ............ 606/61 |
| 2002/0016595 A1 | 2/2002 | Michelson |
| 2002/0045904 A1 | 4/2002 | Fuss et al. |
| 2002/0049444 A1 | 4/2002 | Knox |
| 2002/0055741 A1 | 5/2002 | Schlapfer et al. |
| 2002/0099386 A1 | 7/2002 | Beger et al. |
| 2002/0143328 A1 | 10/2002 | Shluzas et al. |
| 2002/0147449 A1 | 10/2002 | Yun |
| 2002/0161368 A1 | 10/2002 | Foley |
| 2002/0183755 A1 | 12/2002 | Michelson |
| 2002/0188296 A1 | 12/2002 | Michelson |
| 2003/0018389 A1 | 1/2003 | Castro et al. |
| 2003/0040746 A1 | 2/2003 | Mitchell et al. |
| 2003/0045935 A1 | 3/2003 | Angelucci et al. |
| 2003/0074005 A1 | 4/2003 | Roth et al. |
| 2003/0078583 A1 | 4/2003 | Biedermann et al. |
| 2003/0153913 A1 | 8/2003 | Altarac |
| 2003/0187436 A1 | 10/2003 | Bolger et al. |
| 2003/0229347 A1 | 12/2003 | Sherman et al. |
| 2003/0236472 A1 | 12/2003 | Van Hoeck et al. |
| 2004/0018228 A1 | 1/2004 | Fischell et al. |
| 2004/0019263 A1 | 1/2004 | Jutras et al. |
| 2004/0030346 A1 * | 2/2004 | Frey et al. ........................ 606/99 |
| 2004/0044412 A1 | 3/2004 | Lambrecht |
| 2004/0073216 A1 | 4/2004 | Lieberman |
| 2004/0106995 A1 | 6/2004 | Le Couedic et al. |
| 2004/0133207 A1 | 7/2004 | Abdou |
| 2004/0138671 A1 | 7/2004 | Zander et al. |
| 2004/0153070 A1 | 8/2004 | Barker et al. |
| 2004/0167625 A1 | 8/2004 | Beyar et al. |
| 2004/0204712 A1 | 10/2004 | Kolb et al. |
| 2004/0204713 A1 | 10/2004 | Abdou |
| 2004/0249377 A1 | 12/2004 | Kaes et al. |
| 2004/0249379 A1 | 12/2004 | Winslow et al. |
| 2005/0004573 A1 | 1/2005 | Abdou |
| 2005/0010227 A1 | 1/2005 | Paul |
| 2005/0021029 A1 | 1/2005 | Trieu et al. |
| 2005/0021031 A1 | 1/2005 | Foley et al. |
| 2005/0021040 A1 | 1/2005 | Bertagnoli |
| 2005/0033434 A1 | 2/2005 | Berry |
| 2005/0055031 A1 * | 3/2005 | Lim ................................ 606/99 |
| 2005/0085813 A1 | 4/2005 | Spitler et al. |
| 2005/0119747 A1 | 6/2005 | Fabris et al. |
| 2005/0126576 A1 | 6/2005 | Ferree |
| 2005/0131406 A1 | 6/2005 | Reiley et al. |
| 2005/0131421 A1 | 6/2005 | Anderson et al. |
| 2005/0154389 A1 | 7/2005 | Selover et al. |
| 2005/0159813 A1 | 7/2005 | Molz |
| 2005/0171540 A1 | 8/2005 | Lim et al. |
| 2005/0177163 A1 | 8/2005 | Abdou |
| 2005/0192589 A1 | 9/2005 | Raymond et al. |
| 2005/0197660 A1 | 9/2005 | Haid et al. |
| 2005/0203512 A1 | 9/2005 | Hawkins et al. |
| 2005/0203533 A1 | 9/2005 | Ferguson et al. |
| 2005/0203624 A1 | 9/2005 | Serhan et al. |
| 2005/0209694 A1 | 9/2005 | Loeb |
| 2005/0215999 A1 | 9/2005 | Birkmeyer et al. |
| 2005/0234449 A1 | 10/2005 | Aferzon |
| 2005/0234451 A1 | 10/2005 | Markworth |
| 2005/0245928 A1 | 11/2005 | Colleran et al. |
| 2005/0261768 A1 | 11/2005 | Trieu |
| 2005/0273120 A1 | 12/2005 | Abdou |
| 2005/0283153 A1 | 12/2005 | Poyner |

| | | | |
|---|---|---|---|
| 2005/0283245 A1 | 12/2005 | Gordon et al. | |
| 2005/0288669 A1 | 12/2005 | Abdou | |
| 2006/0036240 A1 | 2/2006 | Colleran et al. | |
| 2006/0052870 A1 | 3/2006 | Ferree | |
| 2006/0074488 A1 | 4/2006 | Abdou | |
| 2006/0084977 A1 | 4/2006 | Lieberman | |
| 2006/0084986 A1 | 4/2006 | Grinberg et al. | |
| 2006/0084988 A1 | 4/2006 | Kim | |
| 2006/0111728 A1 | 5/2006 | Abdou | |
| 2006/0142761 A1 | 6/2006 | Landry et al. | |
| 2006/0149238 A1 | 7/2006 | Sherman et al. | |
| 2006/0149278 A1 | 7/2006 | Abdou | |
| 2006/0167454 A1 | 7/2006 | Ludwig et al. | |
| 2006/0184247 A1 | 8/2006 | Edidin et al. | |
| 2006/0195102 A1* | 8/2006 | Malandain | 606/72 |
| 2006/0217710 A1 | 9/2006 | Abdou | |
| 2006/0229614 A1 | 10/2006 | Foley et al. | |
| 2006/0229615 A1 | 10/2006 | Abdou | |
| 2006/0235403 A1 | 10/2006 | Blain | |
| 2006/0247630 A1 | 11/2006 | Lott et al. | |
| 2006/0264942 A1 | 11/2006 | Lim et al. | |
| 2006/0276803 A1 | 12/2006 | Salerni | |
| 2006/0293662 A1 | 12/2006 | Boyer, II et al. | |
| 2007/0032790 A1 | 2/2007 | Aschmann et al. | |
| 2007/0093823 A1 | 4/2007 | Booth et al. | |
| 2007/0093828 A1* | 4/2007 | Abdou | 606/61 |
| 2007/0093829 A1 | 4/2007 | Abdou | |
| 2007/0106383 A1 | 5/2007 | Abdou | |
| 2007/0123884 A1 | 5/2007 | Abdou | |
| 2007/0151116 A1 | 7/2007 | Malandain | |
| 2007/0162000 A1 | 7/2007 | Perkins | |
| 2007/0162001 A1 | 7/2007 | Chin et al. | |
| 2007/0162005 A1 | 7/2007 | Peterson et al. | |
| 2007/0167948 A1 | 7/2007 | Abdou | |
| 2007/0173831 A1 | 7/2007 | Abdou | |
| 2007/0173842 A1 | 7/2007 | Abdou | |
| 2007/0179500 A1 | 8/2007 | Chin et al. | |
| 2007/0225807 A1 | 9/2007 | Phan et al. | |
| 2007/0233077 A1 | 10/2007 | Khalili | |
| 2007/0233082 A1 | 10/2007 | Chin et al. | |
| 2007/0233084 A1 | 10/2007 | Betz et al. | |
| 2007/0270840 A1 | 11/2007 | Chin et al. | |
| 2008/0027545 A1 | 1/2008 | Zucherman | |
| 2008/0183211 A1 | 7/2008 | Lamborne et al. | |
| 2008/0183218 A1 | 7/2008 | Mueller et al. | |
| 2010/0016906 A1 | 1/2010 | Abdou | |
| 2010/0069929 A1 | 3/2010 | Abdou | |
| 2010/0106250 A1 | 4/2010 | Abdou | |

FOREIGN PATENT DOCUMENTS

| | | |
|---|---|---|
| EP | 77159 | 4/1983 |
| EP | 0611116 | 8/1994 |
| EP | 1180348 | 2/2002 |
| EP | 1442715 | 8/2004 |
| FR | 2781359 | 1/2000 |
| FR | 2856271 | 12/2004 |
| WO | WO 2004/032726 | 4/2004 |
| WO | WO 2004/062482 | 7/2004 |
| WO | WO 2004/093702 | 11/2004 |
| WO | WO 2005/077288 | 8/2005 |
| WO | WO 2005/122922 | 12/2005 |
| WO | WO 2006/041963 | 4/2006 |
| WO | WO 2006/058221 | 6/2006 |
| WO | WO 2006/089292 | 8/2006 |
| WO | WO 2006/096756 | 9/2006 |
| WO | WO 2007/041648 | 4/2007 |
| WO | WO 2007/044705 | 4/2007 |
| WO | WO 2007/044836 | 4/2007 |
| WO | WO 2007/056516 | 5/2007 |
| WO | WO 2007/059207 | 5/2007 |
| WO | WO 2008/013960 | 1/2008 |

OTHER PUBLICATIONS

Balderston, R.A., et al., Technique for Achievement and Maintenance of Reduction for Severe Spondylolisthesis Using Spinous Process Traction Wiring and External Fixation of the Pelvis, Spine May 1985:10(4):376-82.

Bostman, O., et al., Posterior spinal fusion using internal fixation with the Daab plate, Acta Orthop Scand Jun. 1984;55(3):310-4.

Deguchi, M., et al., Biomechanical Comparison of Spondylolysis Fixation Techniques, Spine (Phila Pa 1976)Feb. 15, 1999;24(4):328-33.

Denis, F., The Three Column Spine and Its Significance in the Classification of Acute Thoracolumbar Spinal Injuries, Spine Nov.-Dec. 1983; 8(8):817-831.

Derwent English Abstract for French Patent Publication FR 2781359, published Jan. 28, 2000, entitled: "Osteosynthesis frame for spinal surgery has rod with clamps to hold cross bars with anchor screws". Accession No. 9867555.

Derwent English Abstract for French Patent Publication FR 2856271, published Dec. 24, 2004, Osteo-synthesis vertebral column plate, has connection head integrated with plate and movable in three directions of space so as to adapt itself to connection rod, and including opening to facilitate introduction of rod. Accession No. 14694557.

Fischgrund, J.S., et al., 1997 Volvo Award Winner in Clinical Studies, Degenerative Lumbar Spondylolisthesis With Spinal Stenosis: A Prospective, Randomized Study Comparing Decompressive Laminectomy and Arthrodesis With and Without Spinal Instrumentation, Spine (Phila Pa 1976) Dec. 15, 1997;22(24):2807-12.

Heggeness, M.H., et al., Translaminar Facet Joint Screw Fixation for Lumbar and Lumbosacral Fusion; A Clinical and Biomechanical Study,Spine (Phila Pa 1976) Jun. 1991;16(6 Suppl):S266-9.

Korkala, O., et al., Reduction and Fixation of Late Diagnosed Lower Cervical Spine Dislocations Using the Daab Plate: A Report of Two Cases, Arch Orthop Trauma Surg 1984;103(5):353-5.

Neo M, et al., Spinous process plate fixation as a salvage operation for failed anterior cervical fusion, J Neurosurg Spine Jan. 2006;4(1):78-81.

Ozgur, B. et al., Extreme Lateral Interbody Fusion (XLIF): a novel surgical technique for anterior lumbar interbody fusion, Spine J. Jul.-Aug. 2006; 6(4):435-43.

Rapoff, A.J. et al., Biomechanical Comparison of Posterior Lumbar Interbody Fusion Cages, Spine (Phila Pa 1976) Oct. 15, 1997;22(20):2375-9.

Thomsen, K., et al.,1997 Volvo Award winner in Clinical Studies, The Effect of Pedicle Screw Instrumentation on Functional Outcome and Fusion Rates in Posterolateral Lumbar Spinal Fusion: A Prospective, Randomized Clinical Study, Spine (Phila Pa 1976) Dec. 15, 1997;22(24):2813-22.

Voor, M.J., et al., Biomechanical Evaluation of Posterior and Anterior Lumbar Interbody Fusion Techniques, J Spinal Disord Aug. 1998;11(4):328-34.

Wang, J., et al., SPIRE spinous process stabilization plate: biomechanical evaluation of a novel technology. Invited submission from the Joint Section Meeting on Disorders of the Spine and Peripheral Nerves, Mar. 2005, J Neurosurg Spine Feb. 2006;4(2):160-4.

Denis, F. "The three column spine and its significance in the classification of acute, thoracolumbar spinal injuries" Spine Nov.-Dec. 1983; 8(8):817-831.

* cited by examiner

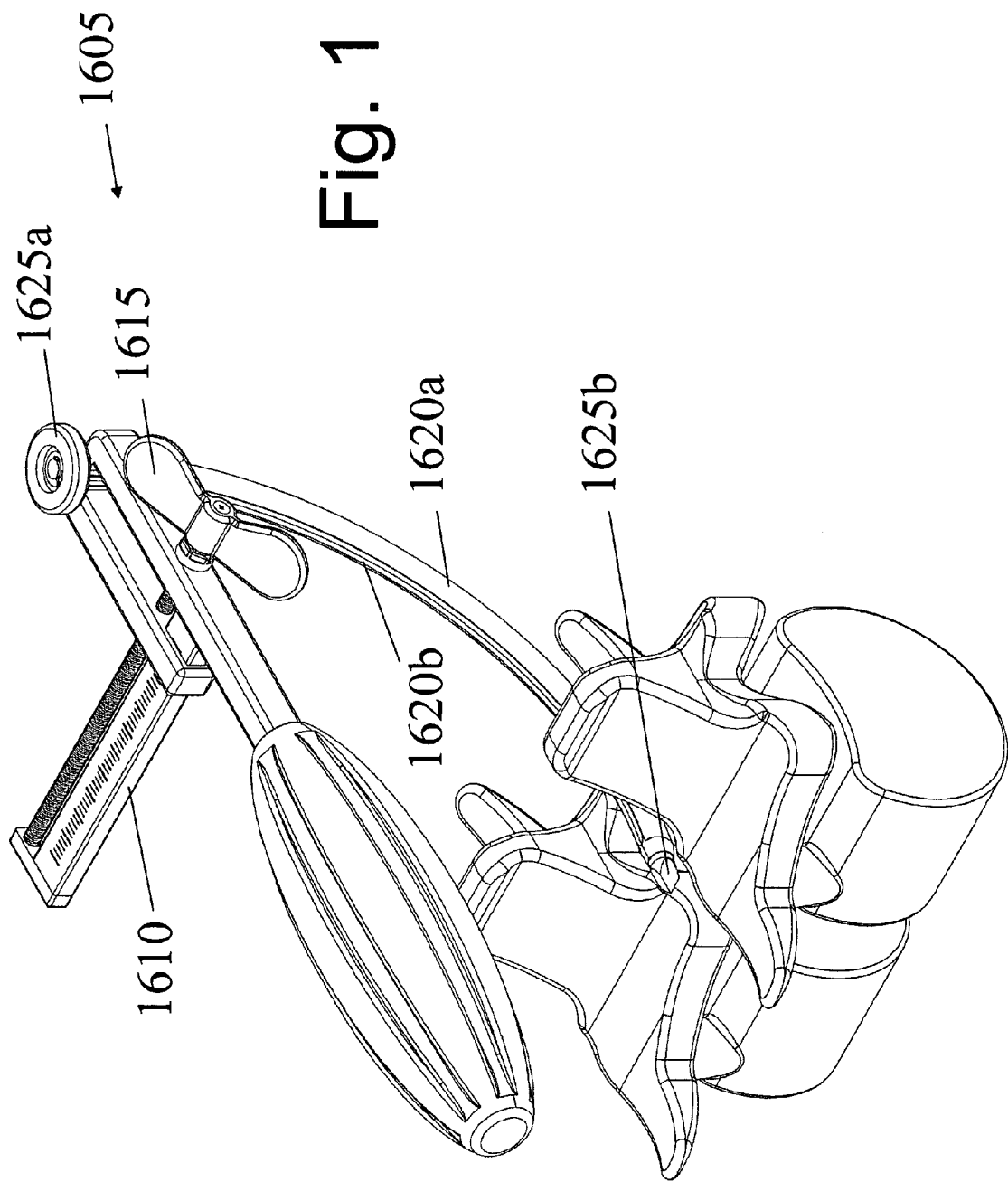

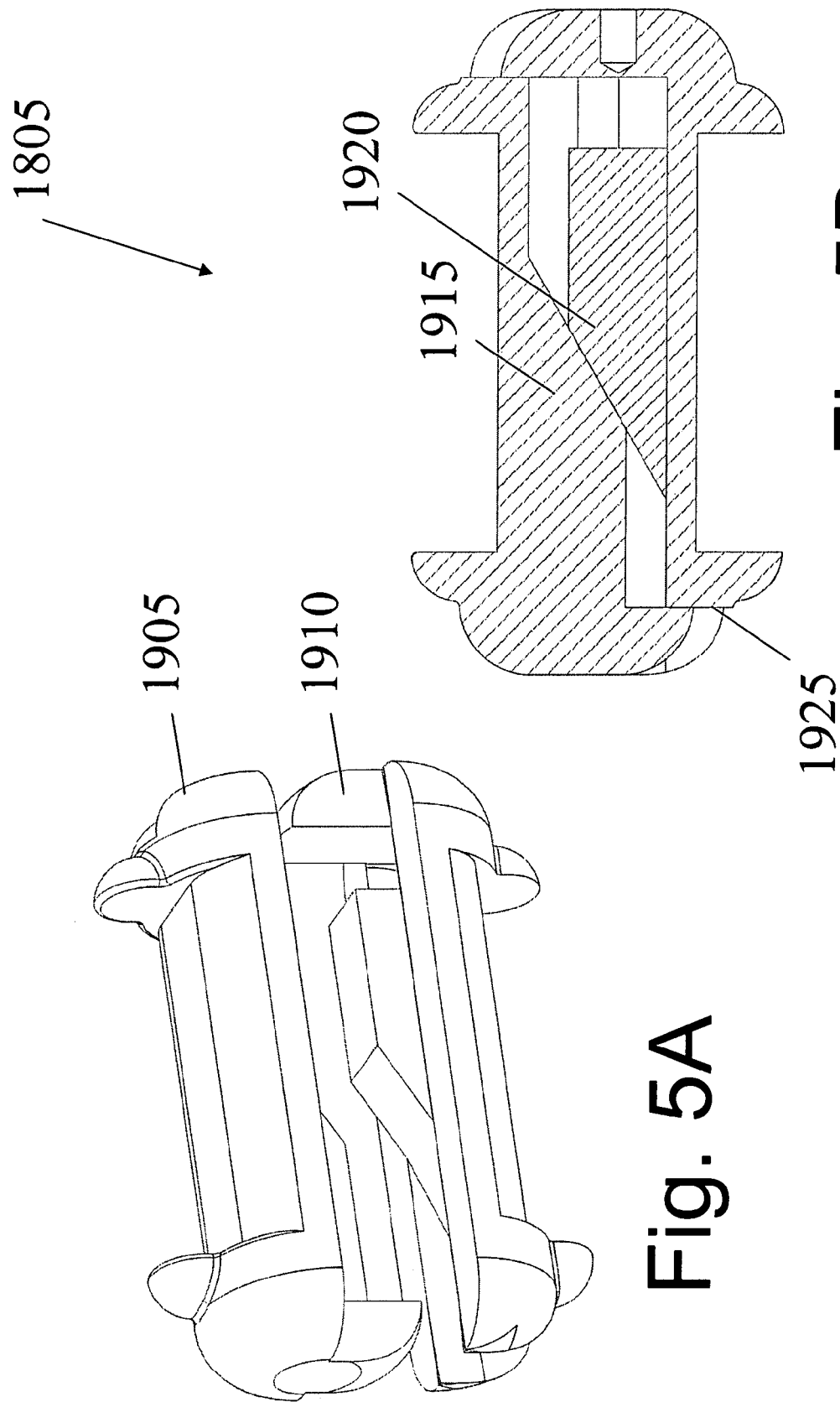

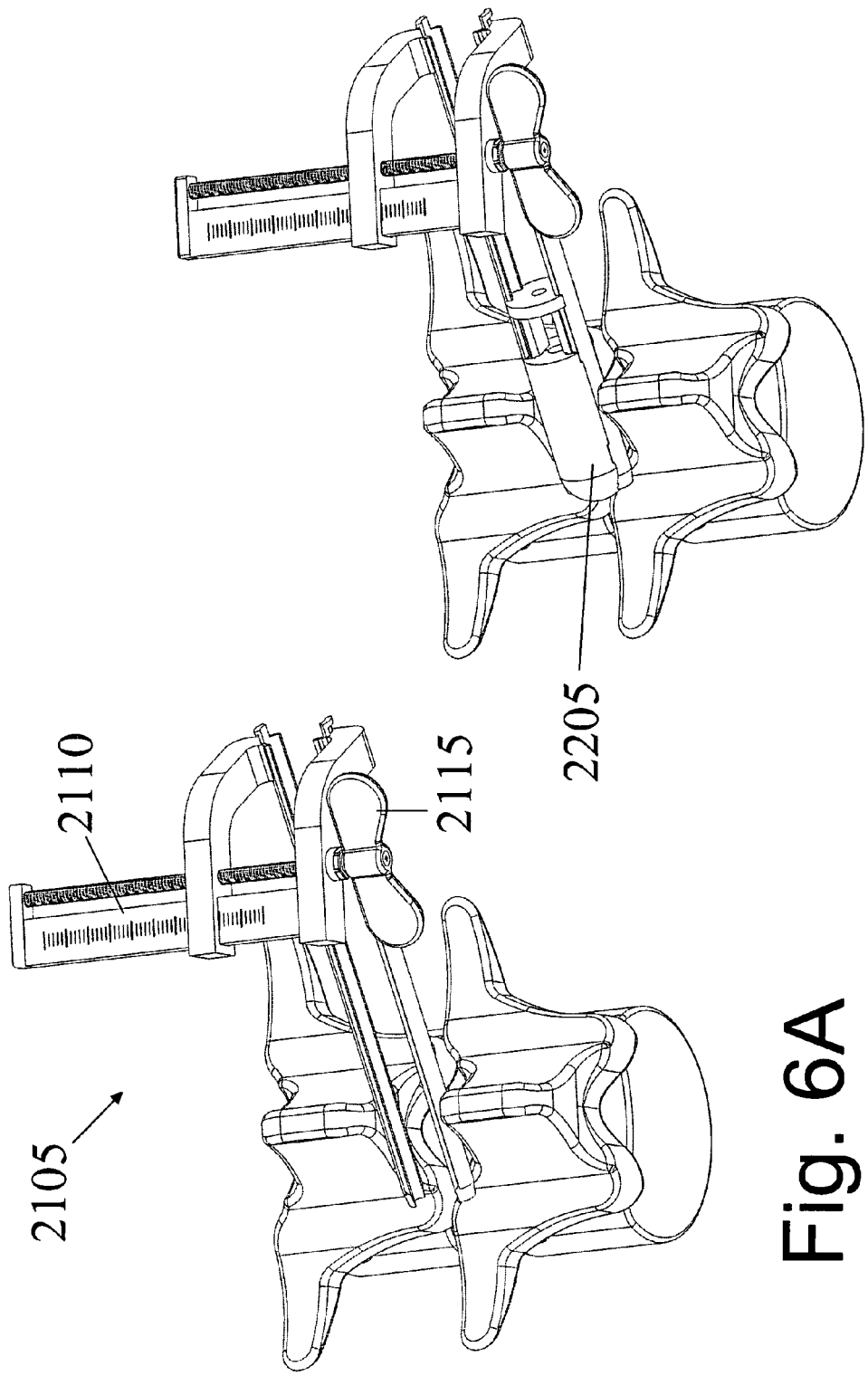

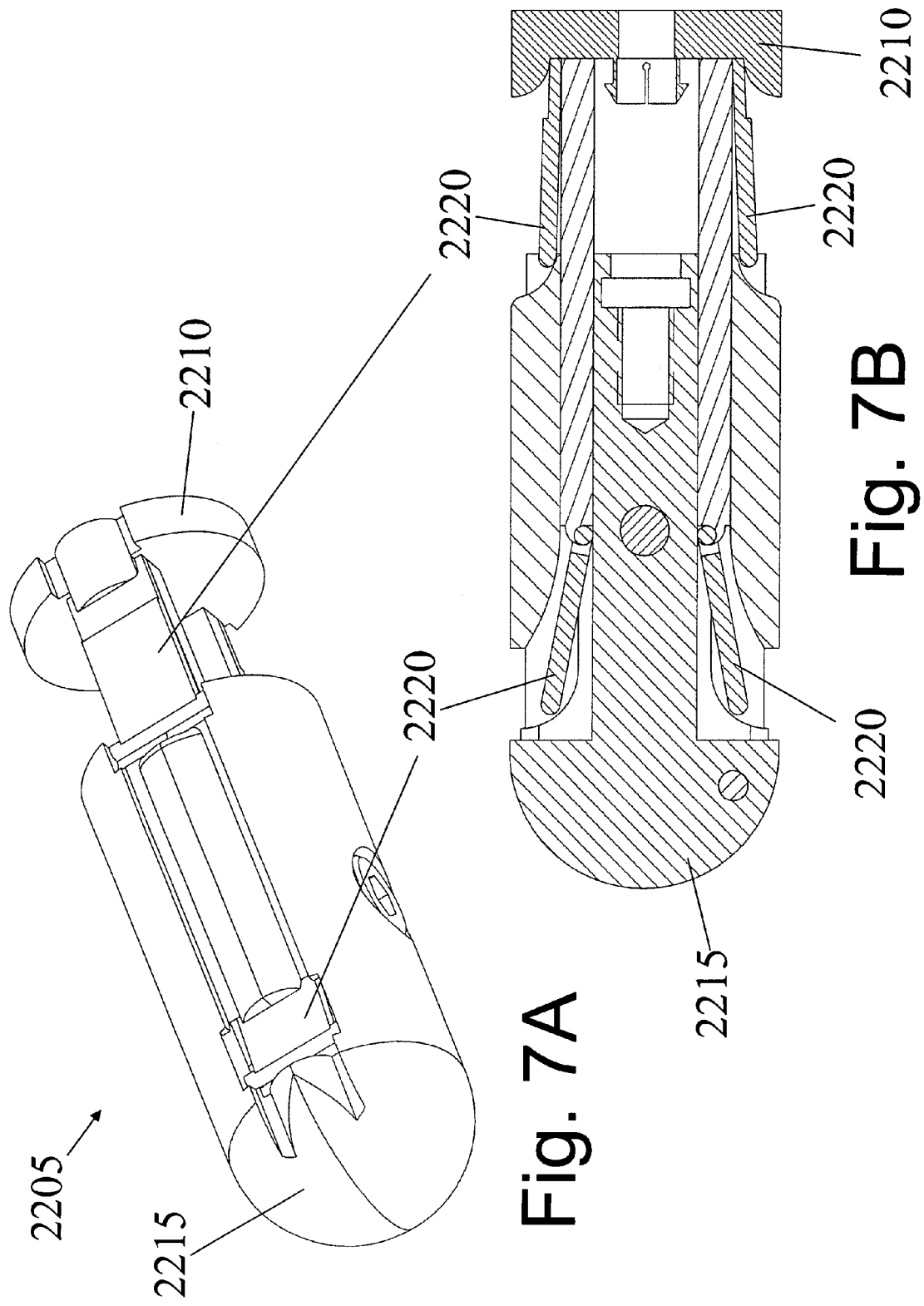

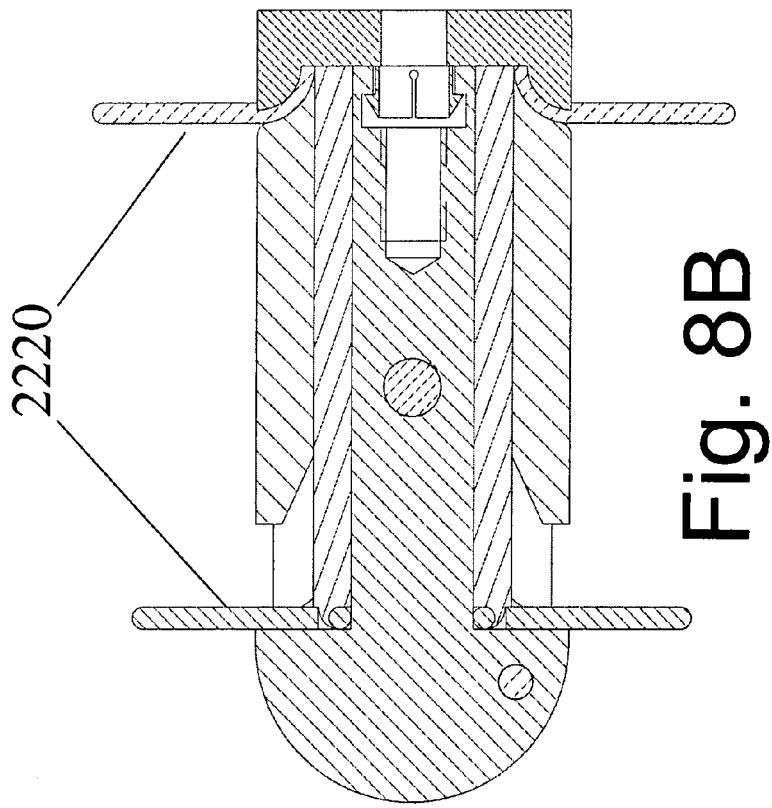
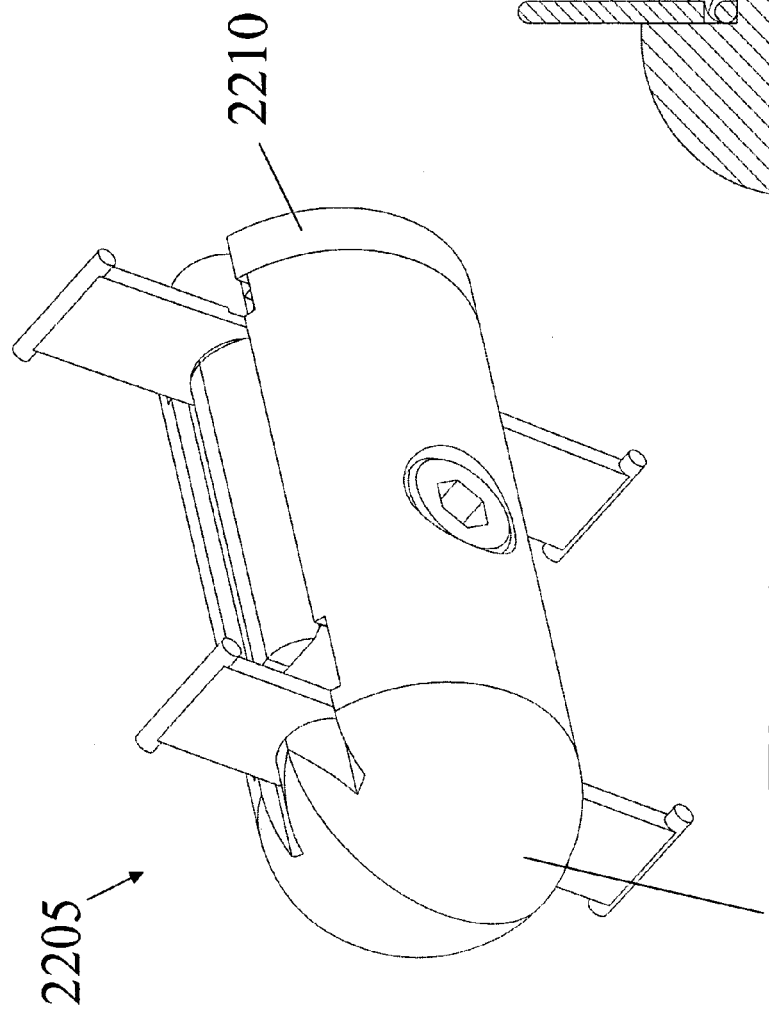
Fig. 8A
Fig. 8B

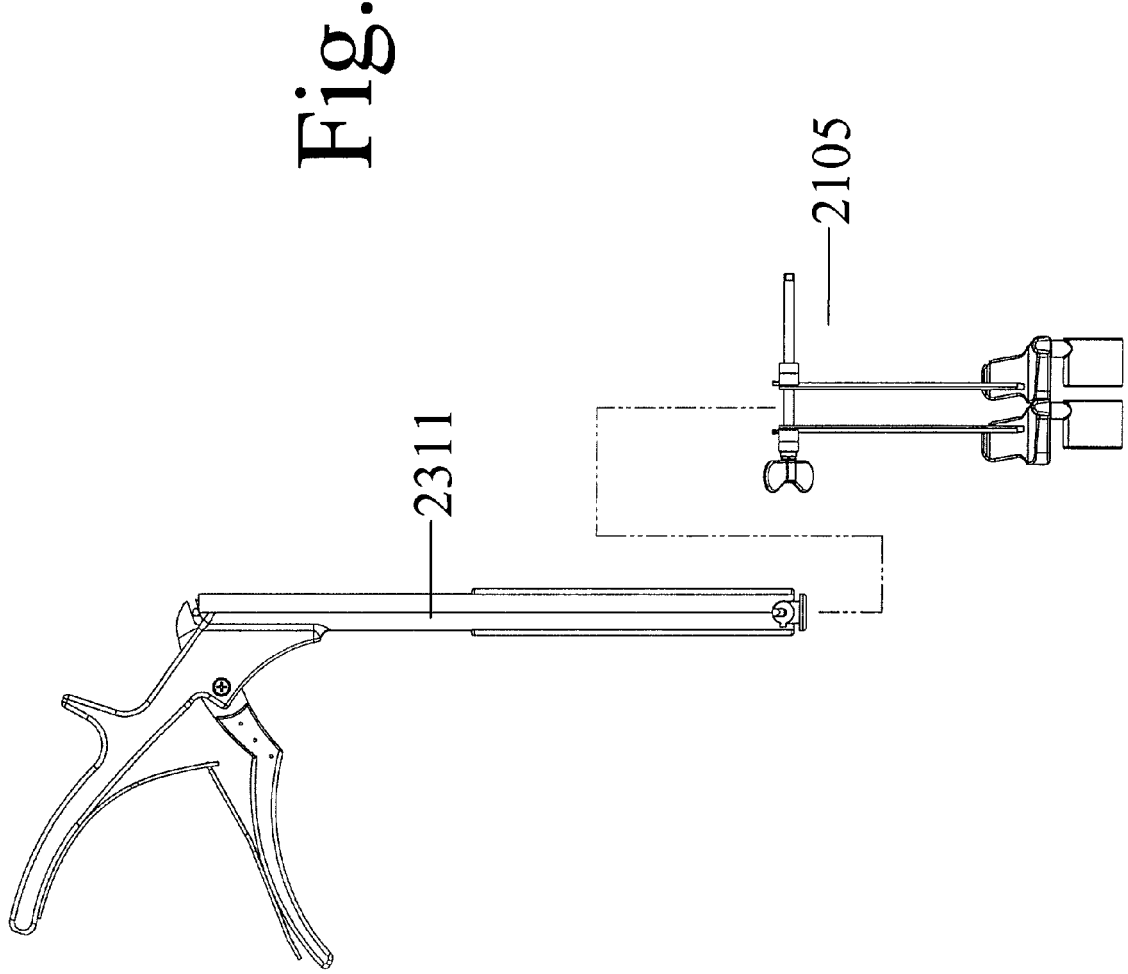

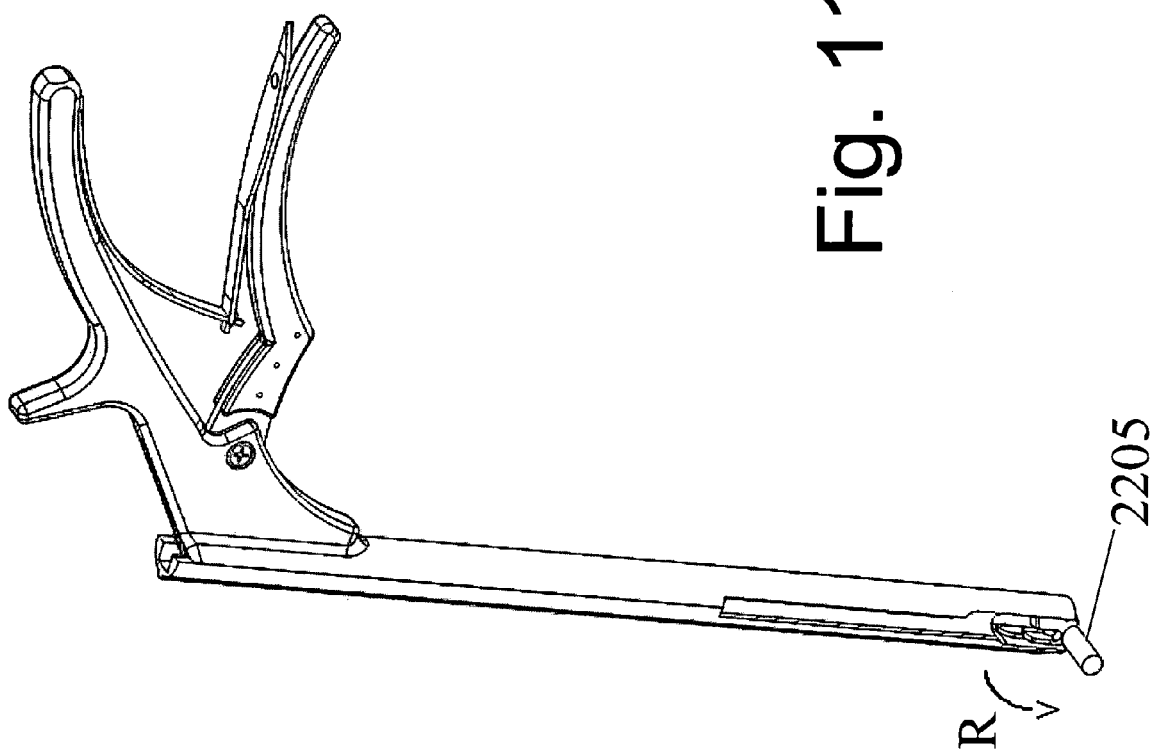

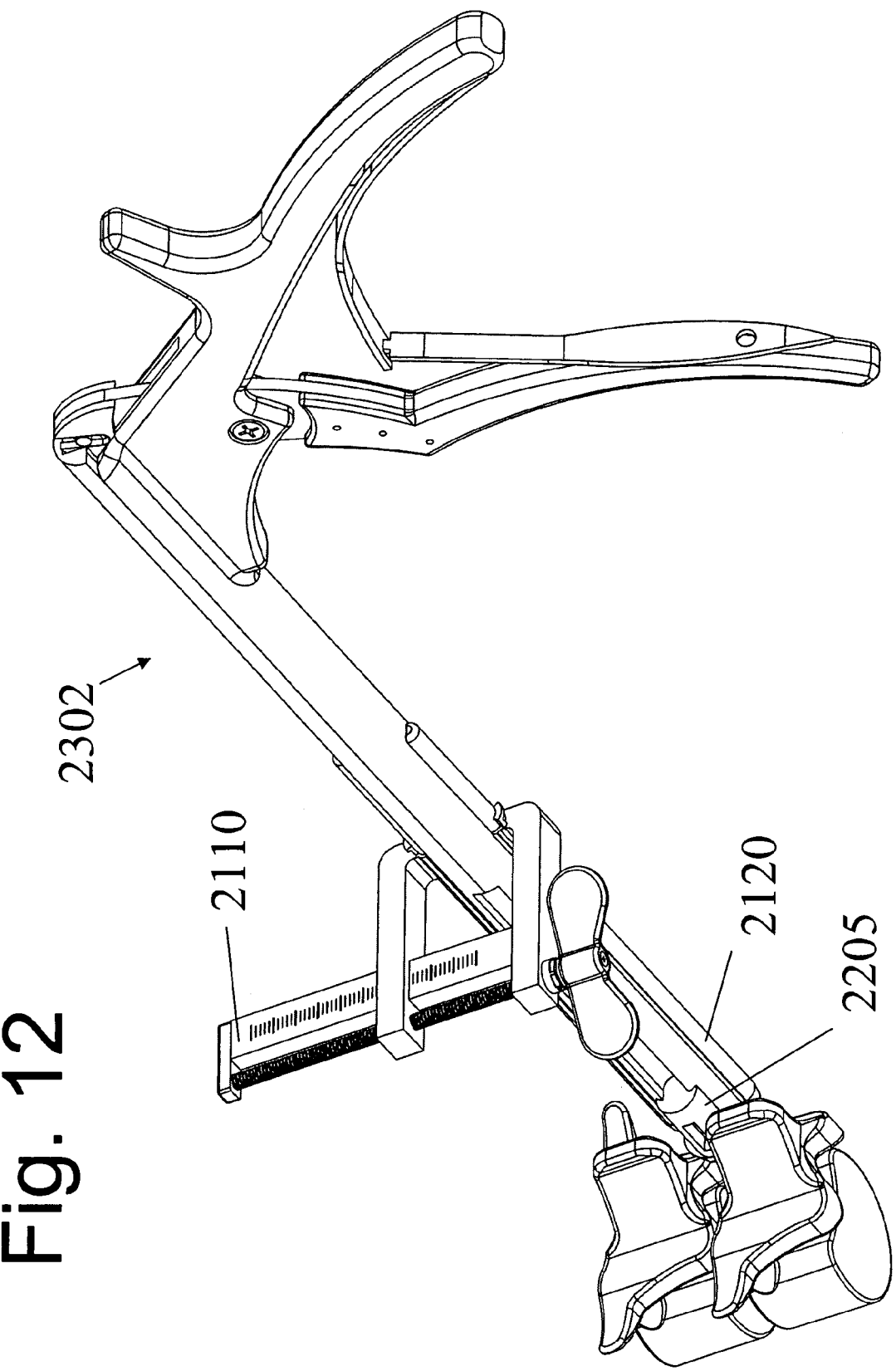

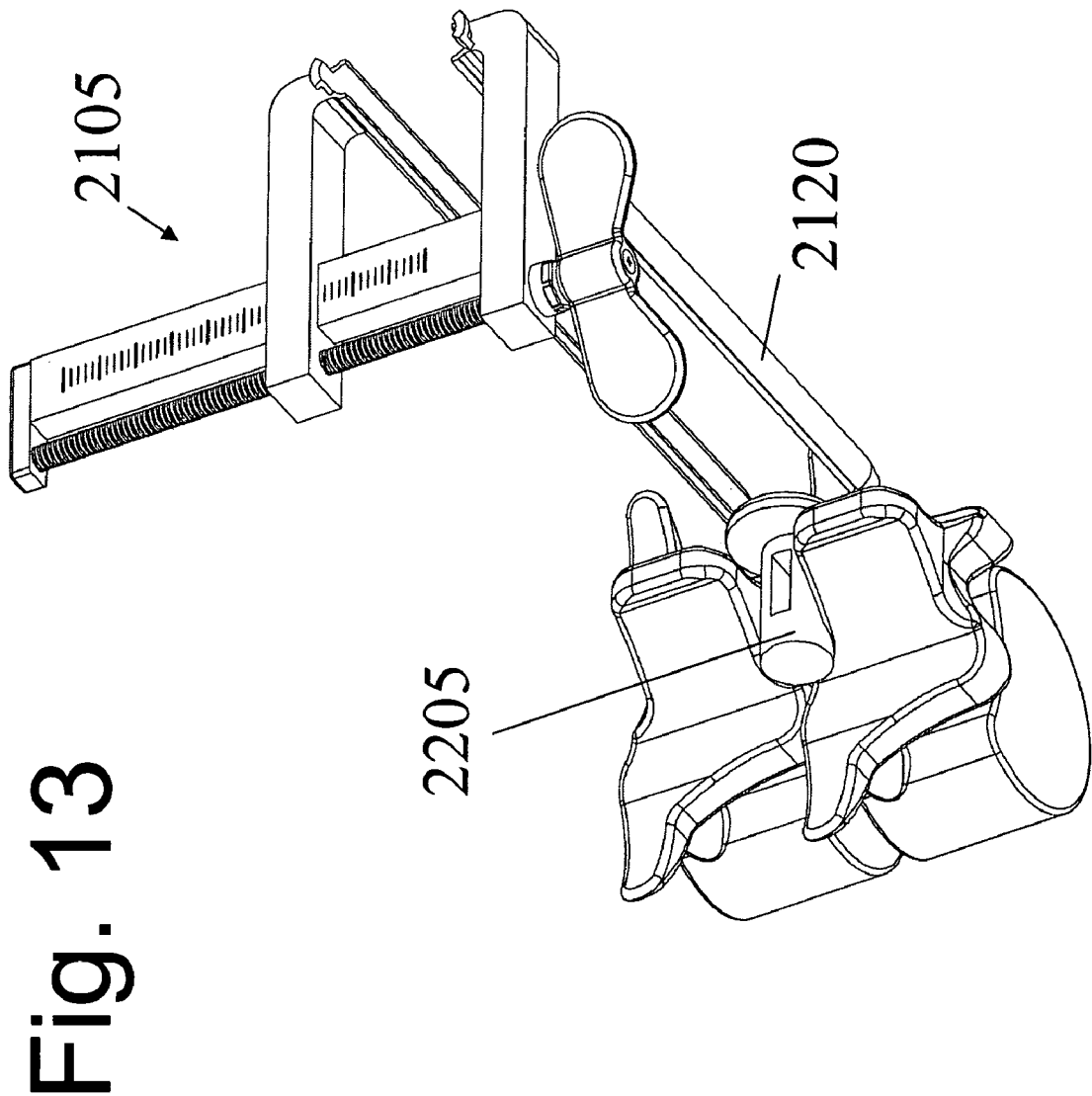

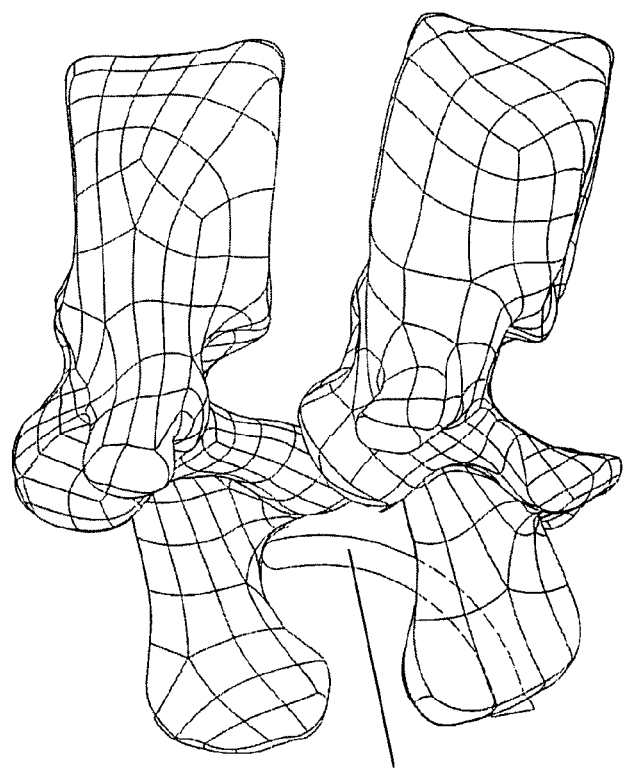
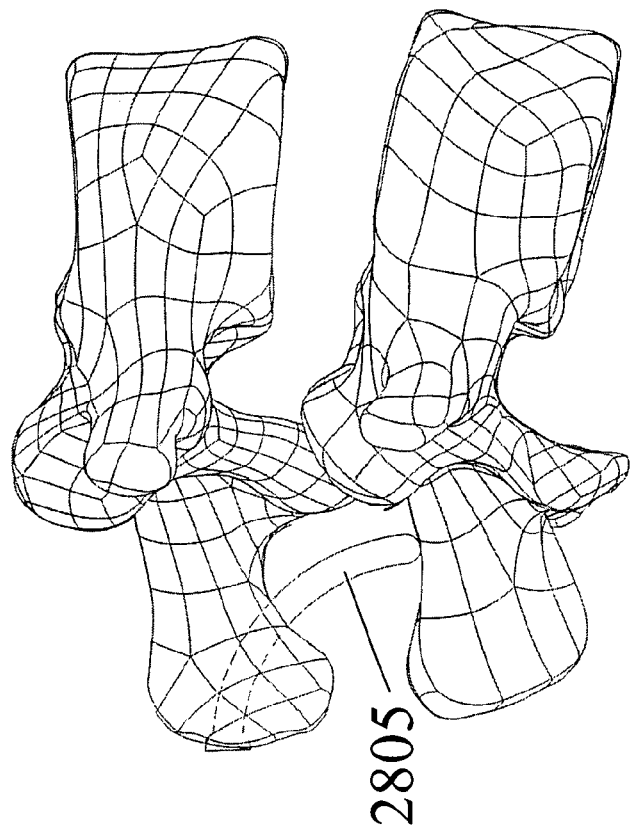
Fig. 14A
Fig. 14B

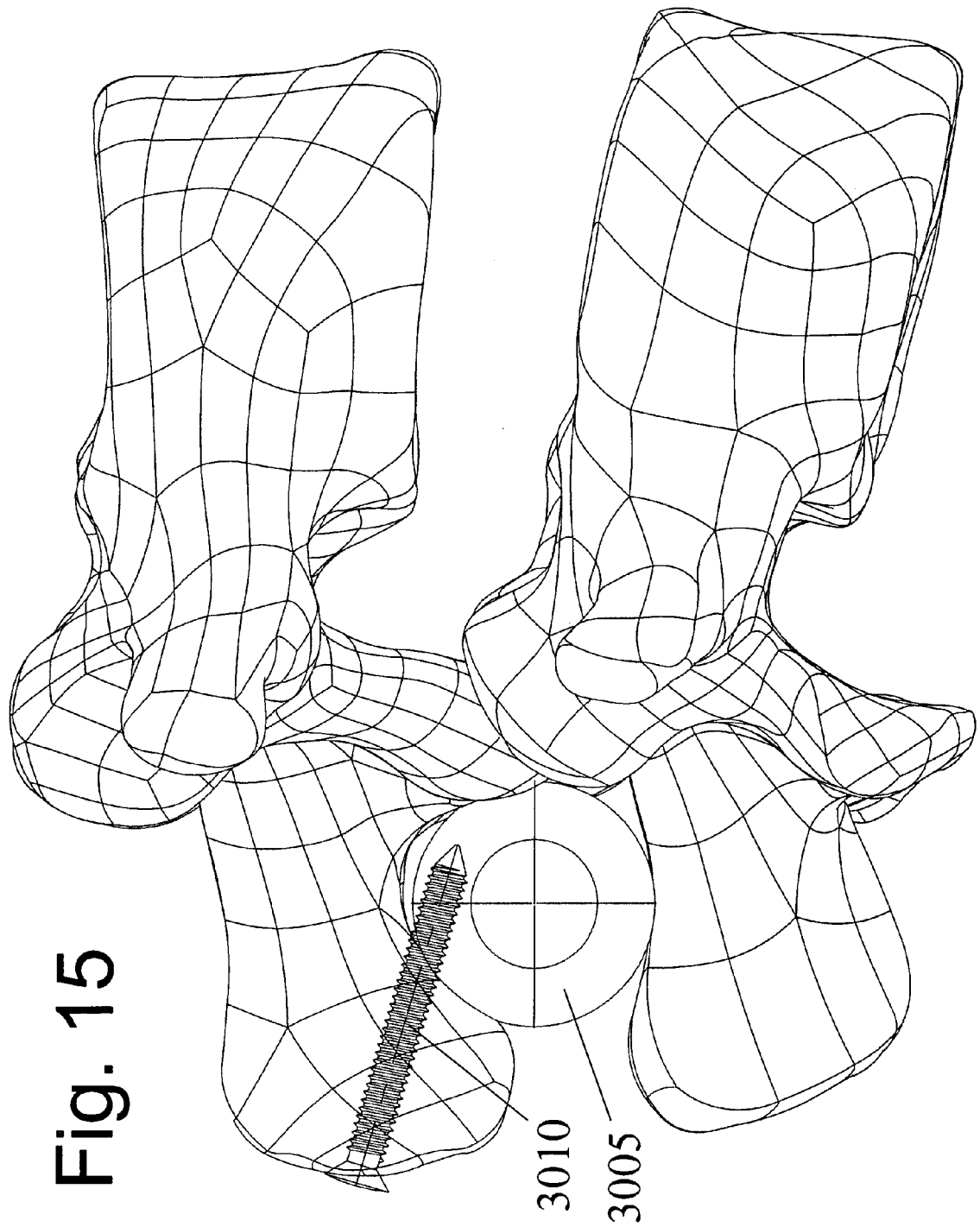

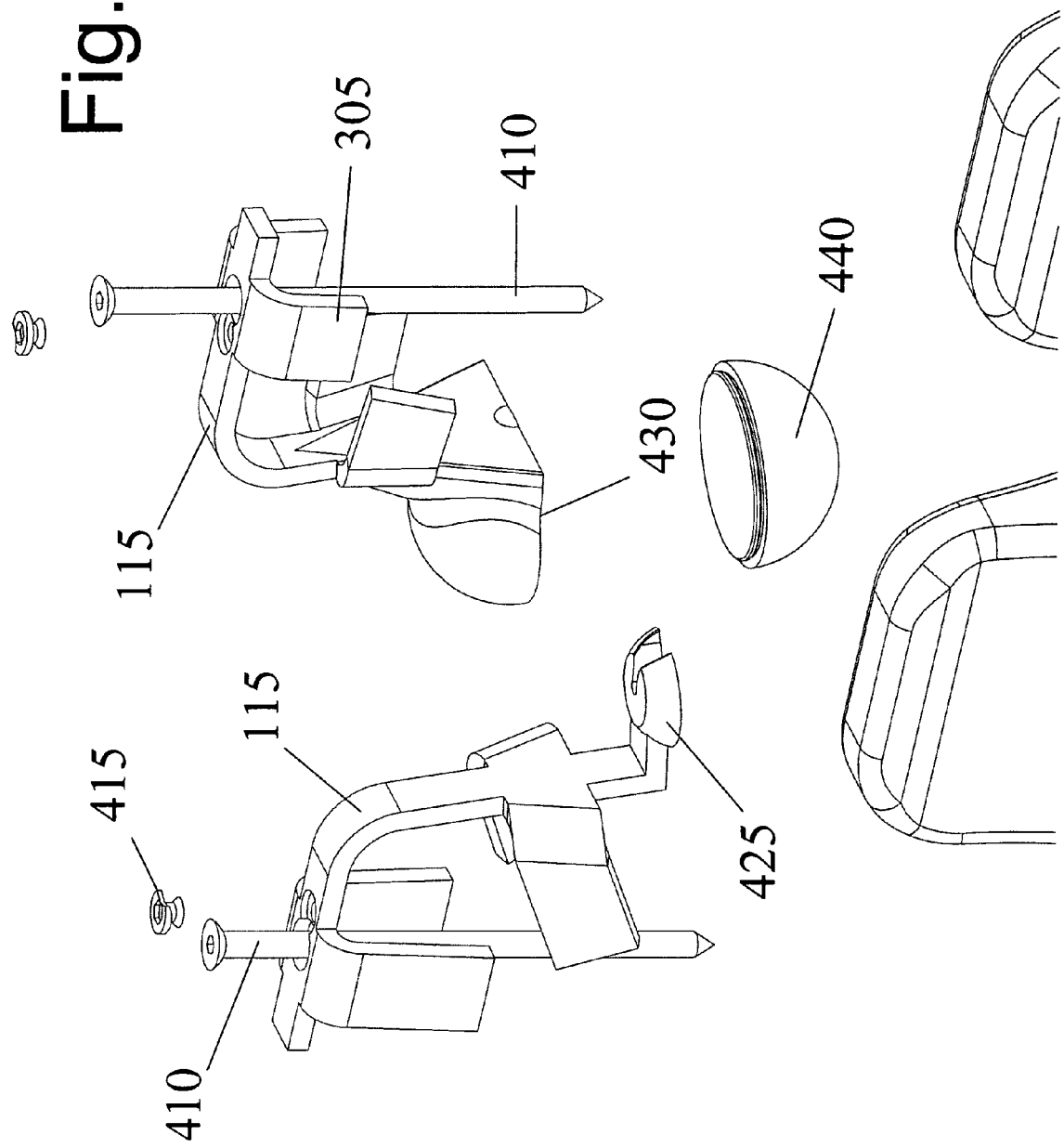

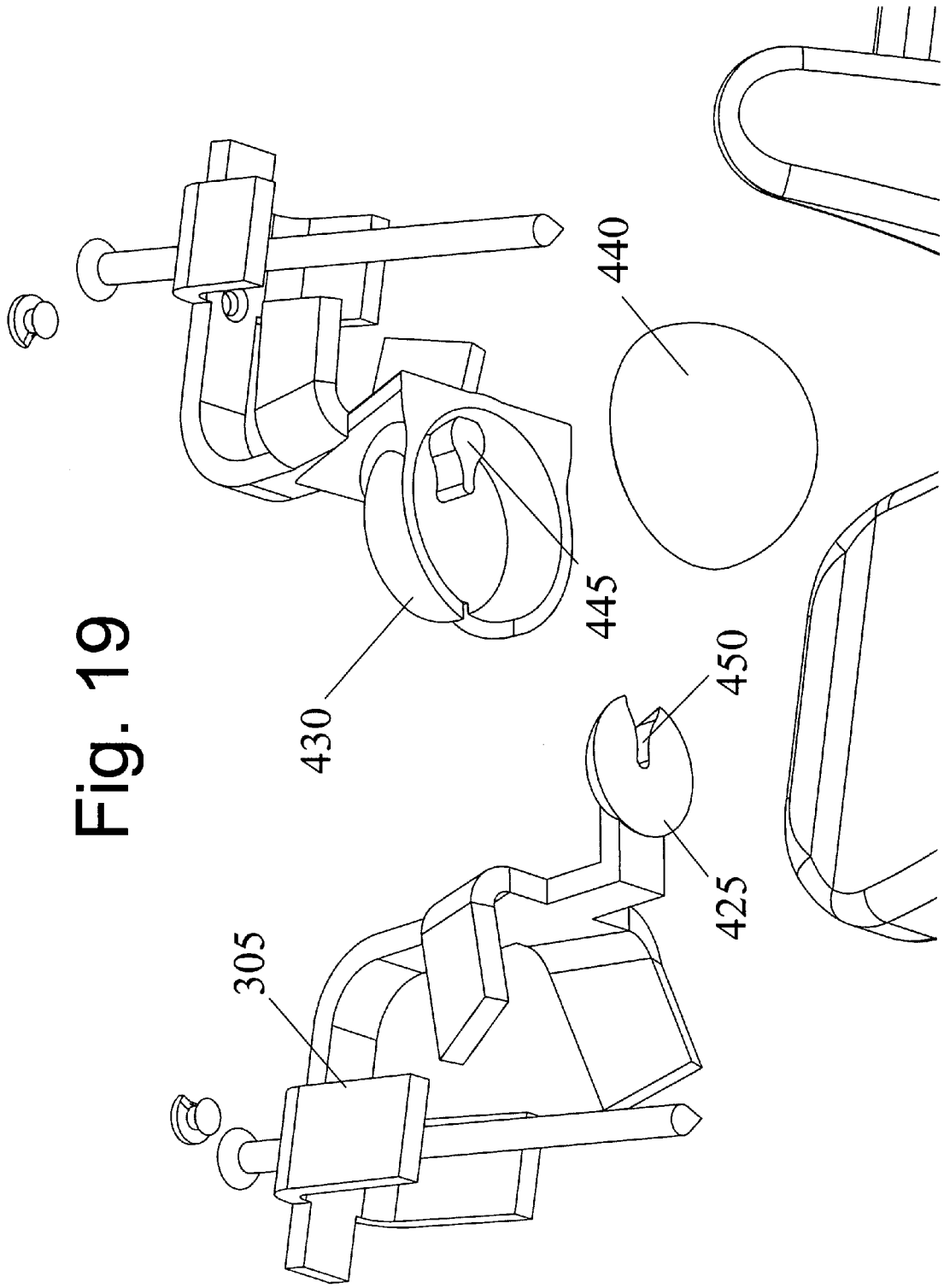

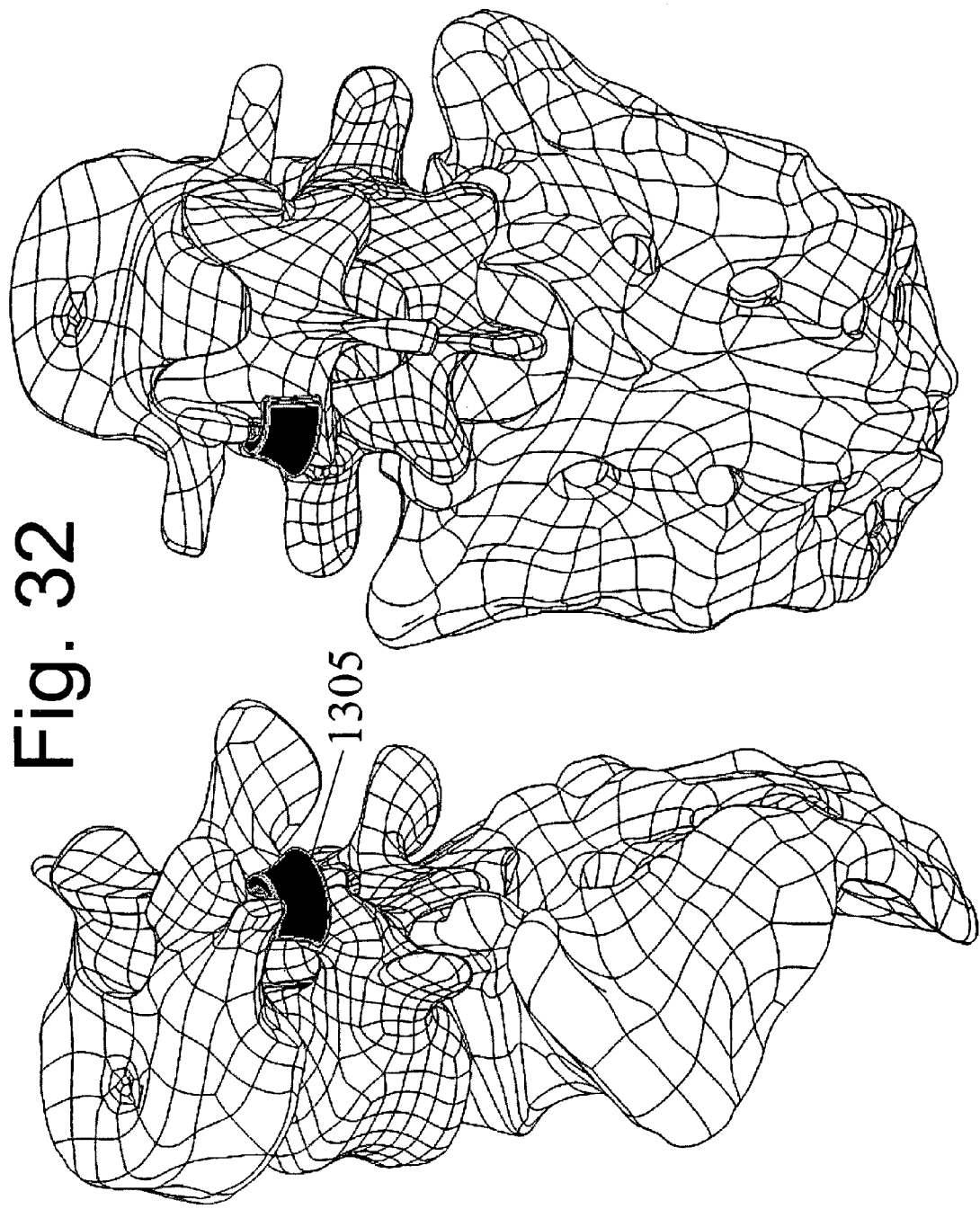

US 8,303,630 B2

DEVICES AND METHODS FOR THE MINIMALLY INVASIVE TREATMENT OF SPINAL STENOSIS

REFERENCE TO PRIORITY DOCUMENTS

This application claims priority of the following U.S. Provisional Patent Applications: (1) U.S. Provisional Patent Application Ser. No. 60/834,209, filed Jul. 27, 2006; (2) U.S. Provisional Patent Application Ser. No. 60/834,003, filed Jul. 28, 2006; (3) U.S. Provisional Patent Application Ser. No. 60/860,942, filed Nov. 24, 2006. Priority of the aforementioned filing dates is hereby claimed. The disclosures of the Non-provisional and Provisional Patent Applications are hereby incorporated by reference in their entirety.

BACKGROUND

The present disclosure is related to orthopedic devices implanted between skeletal segments. The implanted devices are used to adjust and maintain the spatial relationship(s) of adjacent bones. Depending on the implant design, the motion between the skeletal segments may be returned to normal, increased, modified, limited or completely immobilized.

Progressive constriction of the central canal within the spinal column is a predictable consequence of aging. As the spinal canal narrows, the nerve elements that reside within it become progressively more crowded. Eventually, the canal dimensions become sufficiently small-so as to significantly compress the nerve elements and produce pain, weakness, sensory changes, clumsiness and other manifestation of nervous system dysfunction.

Constriction of the canal within the lumbar spine is termed lumbar stenosis. This condition is very common in the elderly and causes a significant proportion of the low back pain, lower extremity pain, lower extremity weakness, limitation of mobility and the high disability rates that afflict this age group.

The traditional treatment for this condition has been laminectomy, which is the surgical removal of the lamina portion of bone and the adjacent ligamentous structures that constrict the spinal canal. Despite advances in surgical technique, spinal decompression surgery can be an extensive operation with risks of complication from the actual surgical procedure and the general anesthetic that is required to perform it. Since many of these elderly patients are in frail health, the risk of developing significant peri-operative medical problems remains high. In addition, the surgical resection of spinal structures may relieve the neural compression but lead to spinal instability in a substantial minority of patients. That is, removal of the spinal elements that compress the nerves may weaken the vertebral column and lead to spinal instability and vertebral mal-alignment. With instability, the vertebrae will move in an abnormal fashion relative to one another and produce pain, nerve re-impingement, weakness and disability. Further, re-stabilization of the spinal column requires additional and even more extensive surgery. Because of these issues, elderly patients with lumbar stenosis must often choose between living the remaining years in significant pain or enduring the potential life-threatening complications of open spinal decompression surgery.

Recently, lumbar stenosis has been treated by the distraction—instead of resection—of those tissues that compress the spinal canal. In this approach, an implantable device is placed between the spinous processes of the vertebral bodies at the stenotic level in order to limit the extent of bone contact during spinal extension. Since encroachment upon the nerve elements occurs most commonly and severely in extension, this treatment strategy produces an effective increase in the size of the spinal canal by limiting the amount of spinal extension. In effect, the distraction of the spinous processes changes the local bony anatomy and decompress the nerves at the distracted level by placing the spinal segment into slight flexion.

Unfortunately, the placement of a conventional interspinous implant requires surgical exposure of the posterior and lateral aspects of the spinous processes as well as the posterior aspect of the spinal column. Since these operations still carry a significant risk of peri-operative complications in the elderly, there remains a need in the field for devices and methods that reduce the scope of the surgical procedure and its inherent risks.

SUMMARY

This application discloses a series of novel devices and methods for the minimally invasive treatment of spinal stenosis. In an embodiment, distraction members are percutaneously placed into the space between two adjacent spinous processes. The distraction members are attached to a distraction platform and the platform is configured to adjustably distract and set the distance between the distraction members. With actuation of the distraction platform, the outer surfaces of the distraction members forcibly abut the spinous processes and distract the adjacent spinous processes away from one another. The inner surface of at least one distraction members forms a guide channel that is adapted to guide and position an orthopedic implant into the distracted interspinous space. The implant is adapted to maintain the increased distance between the spinous processes after removal of the distraction members and distraction platform.

In an alternative embodiment, distraction members are percutaneously placed into the tissues adjacent to the spinous processes and used to introduce an implant-delivery device. The implant is attached to and contained within the delivery device. With actuation, the implant is rotated into the interspinous space and used to forcibly separate the spinous processes.

In another embodiment, a pin or similar anchor is placed at least partially through a first spinous process and positioned so that the distal end abuts a surface of an adjacent spinous process. The pin is used to separate the two adjacent spinous processes and maintain the increased distance between them. In another embodiment, a pin is placed into the base of the superior facet of the lower vertebra and used to limit vertebral extension by preventing the downward travel of the inferior facet of the superior vertebra. Preferably, the pin has a hollow central cavity that accommodates a bone graft or a bone graft substitute and is adapted to fuse with the surrounding bone at the insertion site of the inferior vertebra. Additional embodiments are disclosed that modify the facet joint anatomy and provide direct nerve decompression and/or a limit of vertebral extension.

In another embodiment, an implant is attached onto at least one vertebral bone and adapted to limit the motion of the attached bone relative to an adjacent vertebra. The motion pathway permitted by the implanted is substantially curvilinear and has at least one center of rotation near the natural Instantaneous Axis of Rotation between adjacent vertebrae. Further, the implant permits greater relative motion between the adjacent vertebrae in flexion than it does in extension.

In one aspect, there is disclosed an orthopedic device, comprising a first member adapted to be attached onto at least one vertebra and adapted to limit the motion of the attached vertebra relative to an adjacent vertebra, wherein the first member defines a motion pathway of the attached vertebra, wherein the motion pathway is substantially curvilinear and has at least one center of rotation near a natural instantaneous axis of rotation between the attached vertebra and the adjacent vertebrae and, wherein the first member provides limited relative motion between two vertebrae such that the relative motion is greater in flexion than it is in extension.

In another aspect, there is disclosed a method for the treatment of spinal stenosis in which an orthopedic implant is introduced into a space between the spinous processes of two adjacent vertebras using a minimally invasive surgical technique, comprising: placing two extension members into the space between two adjacent spinous processes of adjacent vertebrae, wherein the extension members are coupled to a distraction platform device capable of adjusting a distance between the extension members; using the distraction platform to separate the extension members, wherein the outer surface of each extension member is adapted to abut a spinous process of each adjacent vertebra so that separation of the extension members by the platform produces an increase in the distance between the adjacent spinous processes, wherein an inner surface of at least one extension members forms a guide channel that is adapted to guide and position an orthopedic implant into the distracted inter-spinous space; placing an orthopedic implant into the space between the two adjacent spinous processes, wherein the implant is adapted to maintain the increase in distance between the adjacent spinous processes after removal of the extension members; and removing the extension members and the distraction platform.

In another aspect, there is disclosed a method for the treatment of spinal stenosis in which an orthopedic implant is introduced into the space between the spinous processes of two adjacent vertebrae using a minimally invasive surgical technique, comprising: positioning two extension members adjacent to, but not into, an inter-spinous space between two adjacent spinous processes, wherein the extension members are coupled to a distraction platform device capable of setting a distance between the extension members; using the distraction platform to separate the extension members, wherein the outer surface of each extension member is adapted to separate tissue adjacent to the inter-spinous space, wherein an inner surface of at least one of the extension members forms a guide channel that is adapted to guide and position an implant delivery device into the tissue adjacent to the inter-spinous space, wherein the implant is adapted to be attached onto the delivery device and be at least partially contained therein, wherein the implant delivery device is adapted to rotate the attached implant about a center point that is substantially contained within the delivery device and through an angle range of 45 to 135 degrees; deploying the implant delivery device onto the extension members, wherein the implant delivery device has an attached orthopedic implant; placing the attached orthopedic implant into the space between the two adjacent spinous processes, wherein the implant is adapted to maintain a distance between the spinous processes after removal of the extension members; and removing the delivery device, extension members and the distraction platform.

In another aspect, there is disclosed a method for the treatment of spinal stenosis, comprising: placing a body of a pin at least partially through a first spinous process such that one end of the pin is positioned to abut a surface of a second, adjacent spinous process that faces the first spinous process; and using the pin to set and maintain a distracted space between the spinous processes.

The implants and methods described permit treatment of spinal stenosis through a minimally invasive surgical procedure. Other features and advantages will be apparent from the following description of various embodiments, which illustrate, by way of example, the principles of the disclosed devices and methods.

BRIEF DESCRIPTION OF THE DRAWINGS

FIG. 1 shows a perspective view of an installer device that is adapted to position an implant in the inter-spinous space between two vertebras.

FIGS. 5A and 5B show perspective and cross-sectional views of an implant, respectively.

FIGS. 6A and 6B show another embodiment of an installer device without and with an exemplary implant, respectively.

FIGS. 7A and 7B show prospective and cross-sectional views of an exemplary implant in the un-deployed state.

FIGS. 8A and 8B show prospective and cross-sectional views of an exemplary implant in the deployed state.

FIG. 9A shows another embodiment of an installer device and an implant delivery instrument.

FIG. 11 shows the linkage mechanism of the implant delivery instrument.

FIG. 12 shows the delivery instrument coupled to the installer device prior to deployment of the implant.

FIG. 13 shows the implant in the inter-spinous space after deployment with the delivery instrument removed.

FIG. 14A shows another embodiment of an implant

FIG. 14B shows an alternative application of the implant.

FIG. 15 shows an implant positioned in a inter-spinous space with a fixation screw anchoring the implant in place.

FIGS. 18 and 19 show exploded views of the device.

FIG. 29A shows a lateral view of the vertebral bodies while

FIG. 32 shows the implant of FIG. 31 placed into the spinal column.

DETAILED DESCRIPTION

FIG. 1 shows a perspective view of an installer device 1605 that is adapted to position an orthopedic implant in the inter-spinous space between the spinous processes of two adjacent vertebras. For clarity of illustration, the vertebral bodies are represented schematically and those skilled in the art will appreciate that actual vertebral bodies include anatomical details not shown in FIG. 1. The device 1605 includes a platform 1610 having an actuator 1615 that can be used to separate a pair of distraction arms 1620a and 1620b. The platform member 1610 may include a scale for measuring the distraction distance or the distraction force. The scale can display the measured distance in a recognized physical unit or as an arbitrary designation (such as, for example, A, B, C, etc.) that is used for implant selection.

Each distraction arm 1620 has a semi-circular inner surface so that, in the non-distracted state, the arms 1620 collectively form an interior circular conduit. A curvilinear trocar with sharpened distal end 1625b and discoid proximal member 1625a is positioned through the circular conduit formed by arms 1620. Discoid proximal member 1625a has locking tabs on its inferior surface that interact with complimentary tabs 1622 of arms 1620 and lock the trocar to the distraction arms. The sharpened end 1625b emerges from the distal end of arms 1620 and, at the time of device insertion, end 1625b divides the skin and soft tissue ahead of advancing arms 1620. Preferably, the distraction arms 1620 are positioned into the inter-spinous space at the stenotic spinal level under x-ray guidance. The trocar is removed and actuator 1615 is rotated to separate the distraction arms and apply a distraction force upon the spinous processes of the two adjacent vertebras.

Figure 3:
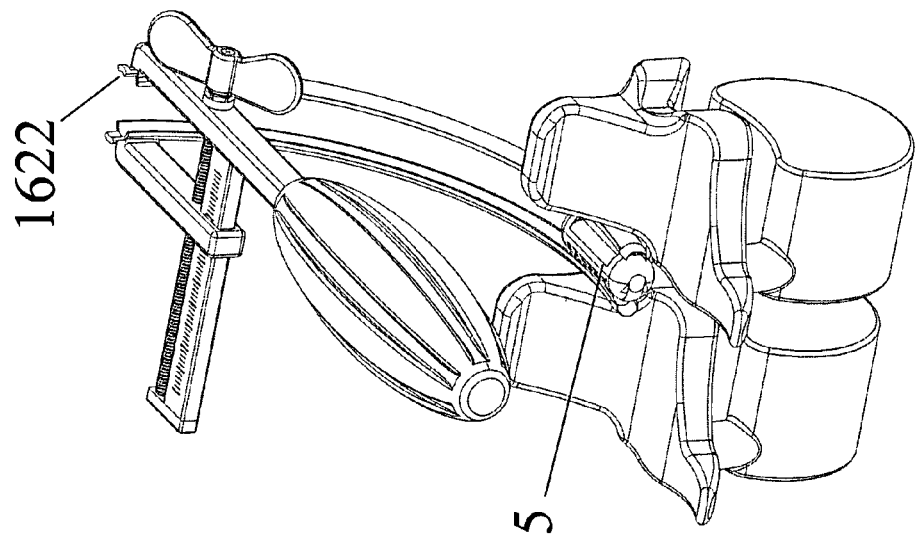
FIG. 3 shows the installer device with an implant at the distal region of the installer arms.
Figure 2:
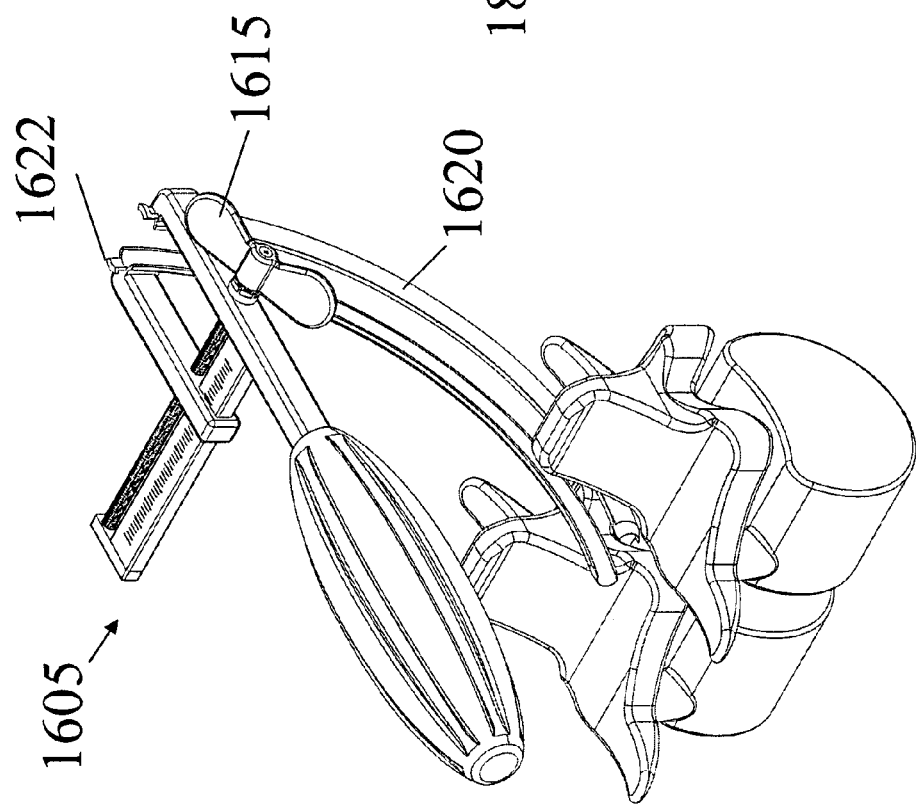
FIG. 2 shows the installer device in a distracted state.

FIG. 2 shows the device 1605 in a distracted state. With rotation of actuator 1615, each distraction arm 1620 is forcibly driven into the spinous process of the adjacent vertebral bone producing distraction of the inter-spinous space. In an embodiment, arms 1620 are curved, although the arms can be also straight or partially curved. A pathway is formed between the separated arms 1620 through which an implant can be driven into the inter-spinous space. The size of the needed implant is given by reading the scale along platform member 1610. FIG. 3 shows the device 1605 with an exemplary implant 1805 positioned at the distal region of the arms 1620. The implant 1805 is inserted into the proximal aspect of the pathway and advanced distally until it rests within the inter-spinous space. The implant is held in place by a placement handle (not shown) and the distraction arms and platform are then removed. Finally, the implant is distracted by actuating the placement handle.

Figure 4:
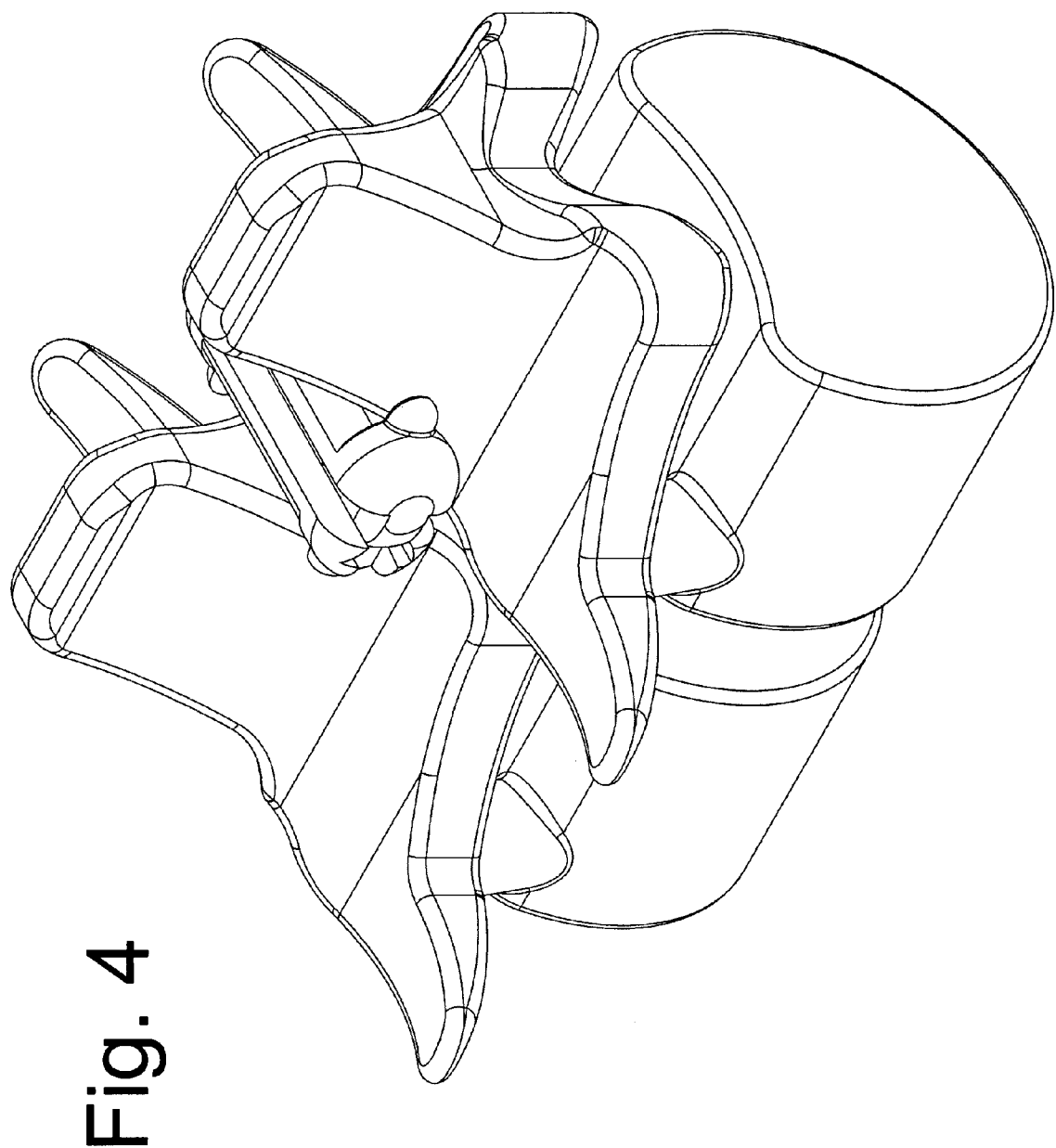
FIG. 4 illustrates an exemplary implant placed within the inter-spinous space.

The implant is shown in FIG. 4 resting within the inter-spinous space. FIGS. 5A and 5B illustrate perspective and cross-sectional views, respectively, of the implant 1805. The implant 1805 includes a first piece 1905 and a second piece 1910 that are movably attached to one another. A pair of wedge-shaped bearing members 1915 form a bearing surface between the two pieces 1905 and 1910. In addition, the pieces 1905 have respective shoulders 1925 that abut one another to guide and limit relative movement therebetween. The bearing members 1915 and the shoulders 1925 guide movement between the two pieces 1905 and 1910 such that the pieces can move and increase the dimensions of the implant 1805.

The implant can be initially delivered into the inter-spinous space in a state of reduces size and then transitioned to the state of enlarged size after it is positioned within the inter-spinous space.

FIGS. 6A and 6B show another embodiment of an installer device 2105. The device 2105 includes a platform 2110 having an actuator 2115 that can be used to separate a pair of distractor arms 2120. In this embodiment, the distractor arms are straight. As discussed below, the arms 2110 can be used as a guide for positioning an implant 2205 into the inter-spinous space (FIG. 6B)

FIGS. 7A and 7B show perspective and cross-sectional views of an exemplary implant 2205 in the un-deployed state. Implant 2205 contains at least longitudinal tract 2207 that interacts with the inner aspect of arms 2210. The implant 2205 includes first and second members 2210 and 2215 that are movably attached. When the members 2210 and 2215 are moved toward one another, one or more pivotably mounted arms 2220 are moved to a position that extends outwardly from the implant 2205. The arms can be moved to the extended position after implantation in the inter-spinous space. FIGS. 8A and 8B show perspective and cross-sectional views of an exemplary implant 2205 in the deployed state. Note that the distal arms 2220 have a bearing articulation with the deploying portion of member 2210 while the proximal arms 2220 have a deformable base that is integrally attached to member 2210. Either mechanism may be employed on any of mounted arms 2220.

Figure 9B:
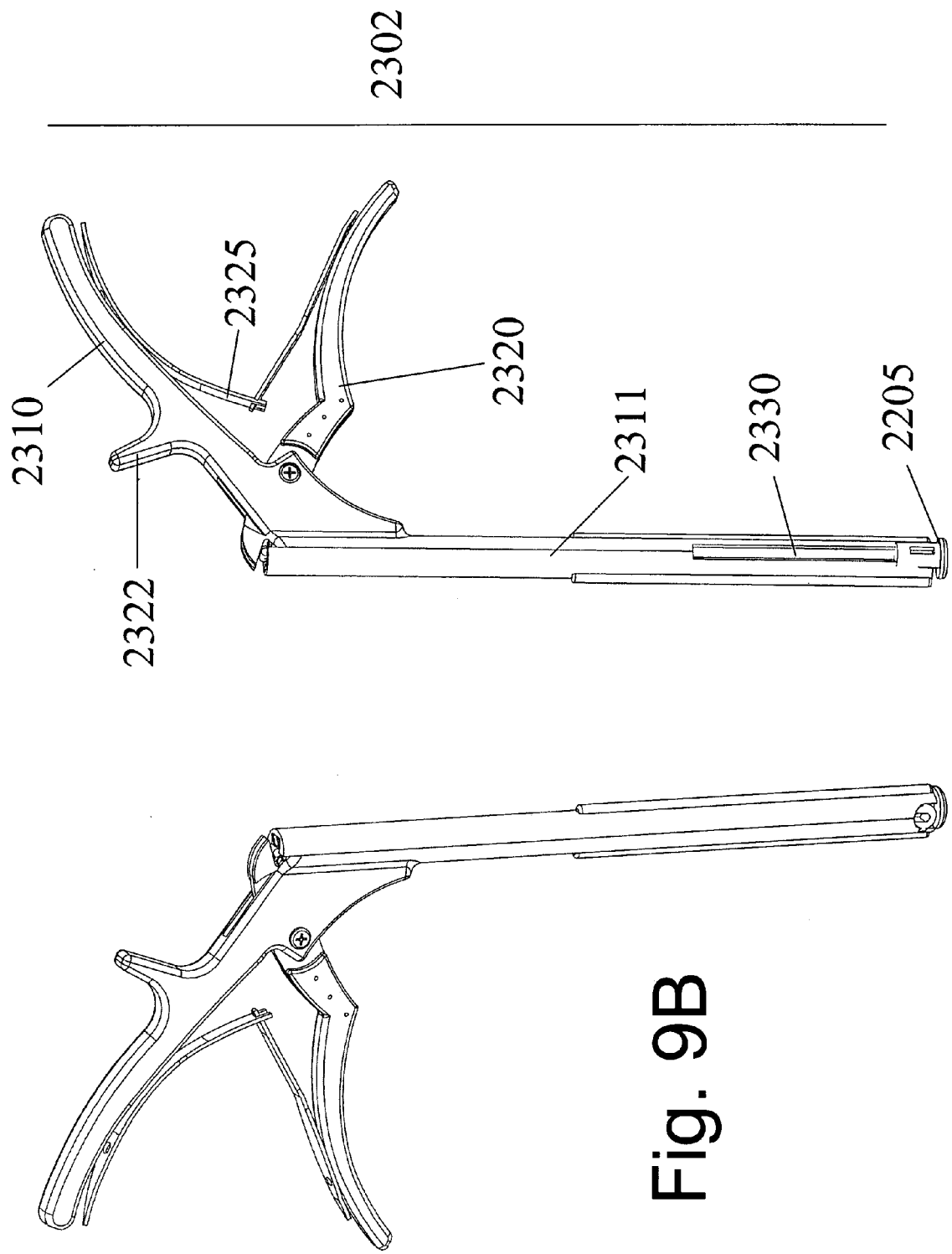
FIG. 9B shows perspective views of an implant delivery instrument.

FIG. 9A illustrates an additional embodiment. A distraction platform with straight distraction arms is percutaneously positioned under x-ray guidance. The arms are placed lateral to the inter-spinous space. A delivery instrument 2303 is attached to the implant and used to place the implant into the inter-spinous space. FIG. 9B shows perspective views of the delivery instrument 2302. In the illustrated embodiment, the instrument 2302 includes a two-piece handle having a first arm 2310 and a second arm 2320 that is movably mounted relative to the first arm 2310 in a pivot or trigger fashion. The first and second arms are ergonomically arranged such that an operator can grasp the arms using a single hand. For example, the first arm 2310 is sized and shaped to support an operator's palm and thumb such as on a thumb grip 2322. Likewise, the second arm 320 can be grasped by the operator's fingers to pull the second arm 2320 toward the first arm 2310 and actuate the instrument 2302. A biasing member 2325 is interposed between the first and second arms. It should be appreciated that the instrument can be actuated with other mechanisms and need not use a two-piece handle configuration.

Figure 10:
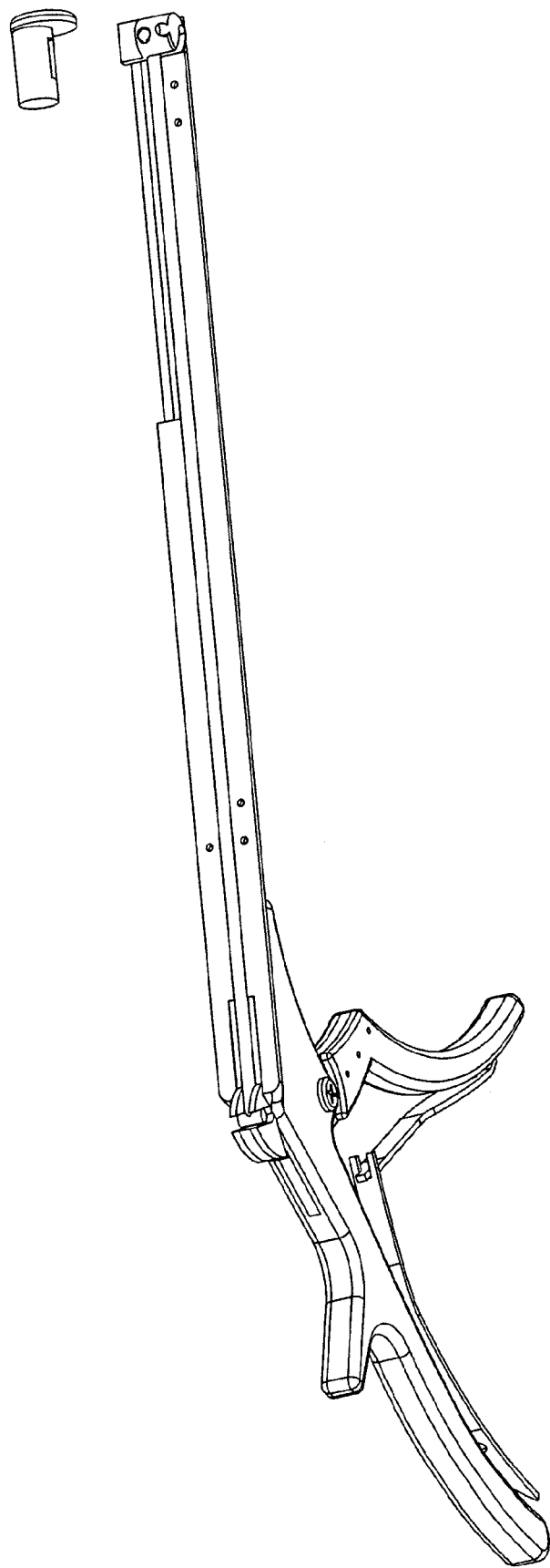
FIG. 10 shows the delivery instrument after actuation such that an implant has rotated to a deployment position.

With reference still to FIG. 9B, a housing 2311 extends outward from the handle. The housing 2311 is sized and shaped to contain the implant 2205. In the illustrated embodiment, the housing 2311 has an elongated, tube-like shape and is partially hollow so as to contain the implant 2205 as well as an internal actuation mechanism that expels the implant from the housing. A slot 2330 is located at or near a distal end of the housing 2311. The slot communicates with an internal cavity in the housing 2311 in which the implant 2205 resides. The slot is sufficiently long and wide such that the implant 2205 can pass through the slot during deployment of the implant. FIG. 10 illustrates the internal mechanism of the placement device. FIG. 11 shows the instrument 2302 after actuation such that the implant 2205 has rotated (as represented by the arrow R) to a deployment position.

FIG. 12 shows the delivery instrument 2302 coupled to the installer device 2105 prior to deployment of the implant 2205. The elongated housing 2311 is placed in between the distractor arms 2120 such that a distal end of the housing 2311 is lateral to the inter-spinous space between the vertebrae. The delivery instrument is then actuated to rotate the implant 2205 into the inter-spinous space. FIG. 13 shows the implant 2205 in the inter-spinous space after removal of delivery instrument 2302.

FIG. 14A shows another embodiment of an implant. In this embodiment, the implant comprises a curved pin or screw 2805 that is sized and shaped to be passed through the spinous process of a vertebrae. The screw 2805 has a curved contour that permits a portion of the screw to extend through the spinous process with a distal region of the screw extending through the inter-spinous space. A proximal end of the screw 2805 is positioned at the exterior of the spinous process. The distal end of the screw 2805 abuts a surface of the spinous process of the adjacent vertebra. The pin may be at least partially comprised of a bone graft or bone graft substitute so as to fuse with the spinous process in which it is embedded. The pin maybe embedded in a first spinous process and abut a second spinous process, as shown in FIG. 14A, or it may be alternatively embedded in the second spinous process and abut the first spinous process, as shown in FIG. 14B.

FIG. 15 shows an implant positioned in an inter-spinous space and affixed to the spine with a fixation screw 3010. The implant 3005 is positioned within the disc space such that outer surface of the implant abuts adjacent vertebrae. A fixation screw 3010 extends through the spinous process and into the implant 3005. The screw may be at least partially comprised of a bone graft or bone graft substitute so as to fuse with the spinous process in which it is embedded. If the interior aspect of implant 3005 is also at least partially comprised of a bone graft or bone graft substitute, then screw 3010 can fuse with both the spinous process and implant 3005. This provides a bone bridge between the implant 3005 and the spinous process without direct fusion of the implant onto the spinous process.

Figure 17:
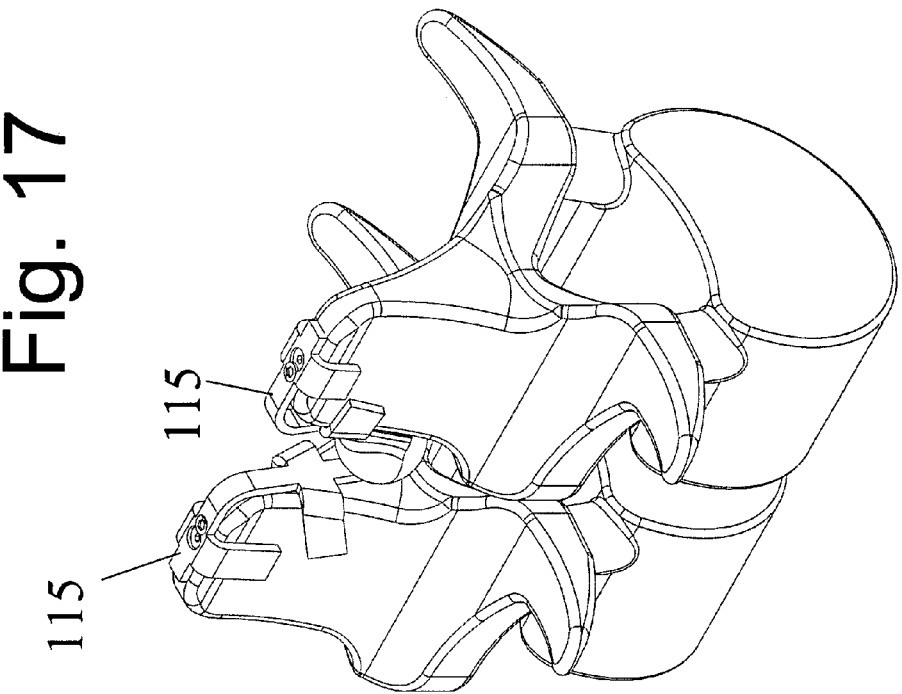
FIGS. 16 and 17 show perspective views of a device that is configured for placement between the spinous processes of two adjacent vertebras.
Figure 16:
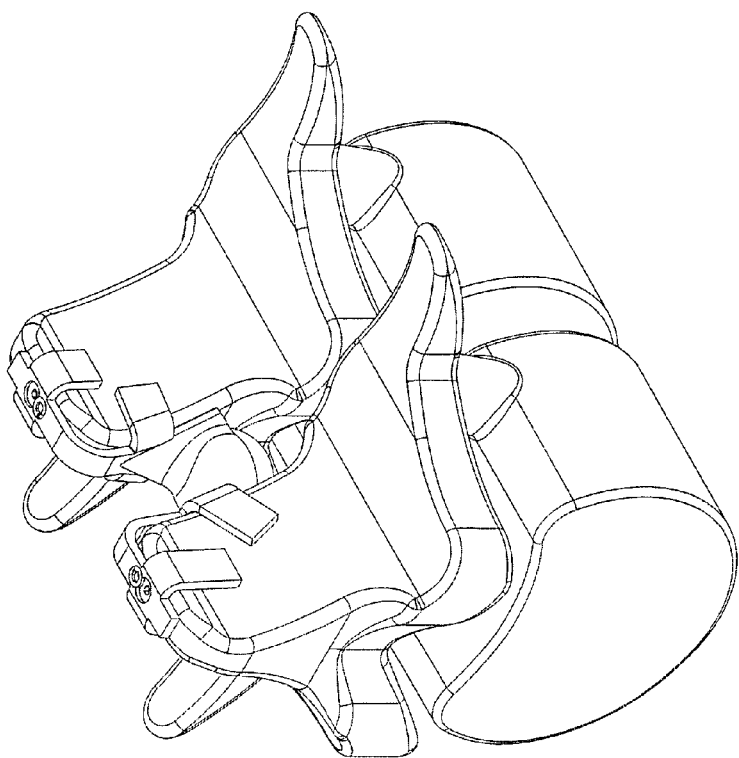

FIGS. 16 and 17 show perspective views of a device 105 that is configured for placement between the spinous processes of two adjacent vertebral bodies. The device 105 includes a spacer region or central region 110 that is sized and shaped to fit between the spinous processes of the two adjacent vertebral bodies. The device 105 further includes a pair of attachment members 115 that are adapted to attach and anchor onto the spinous process of at least one of the vertebral bodies. The central region 110 can have a variety of shapes and sizes for placement between the spinous processes. The attachment members 115 can also have various sizes and shapes for attachment to the spinous processes.

FIGS. 18 and 19 show exploded views of the device 105. The device 105 includes attachment members 115 that are adapted to attach and anchor onto the spinous process of at least one of the vertebral bodies. Each attachment member 115 has a pair of downwardly-extending arms 305 that are sized to receive a spinous process therebetween. An upper portion of the attachment member 115 is sized and shaped to sit over the spinous process. The upper portion has a borehole that is sized to receive a threaded screw 410 during implantation. A locking mechanism 415 can be within the attachment member 115 to serves to prevent unwanted movement and/or back out of the screw 410. While illustrated as a locking cam, the locking mechanism 415 may include any locking mechanism known in the art.

A first bearing member 425 has a rounded articulating surface that is adapted to interact with a complimentary articulating surface on a second bearing member 430. The member 425 is sized and shaped to be received in a cavity inside the member 430 so as to permit at least some rotational movement therebetween. A third bearing member 440 is at least partially dome-shaped and is adapted to couple to the members 425 and 430. In particular, the member 440 mates with the member 430 such as through a threaded engagement.

With reference still to FIGS. 18 and 19, member 430 includes a protrusion 445 that is sized and shaped to mate with an indentation 450 in the member 425. In the assembled device, the interaction of protrusion 445 and indentation 450 serves to limit the amount of rotation and lateral flexion between the members 425 and 430.

Figure 20:
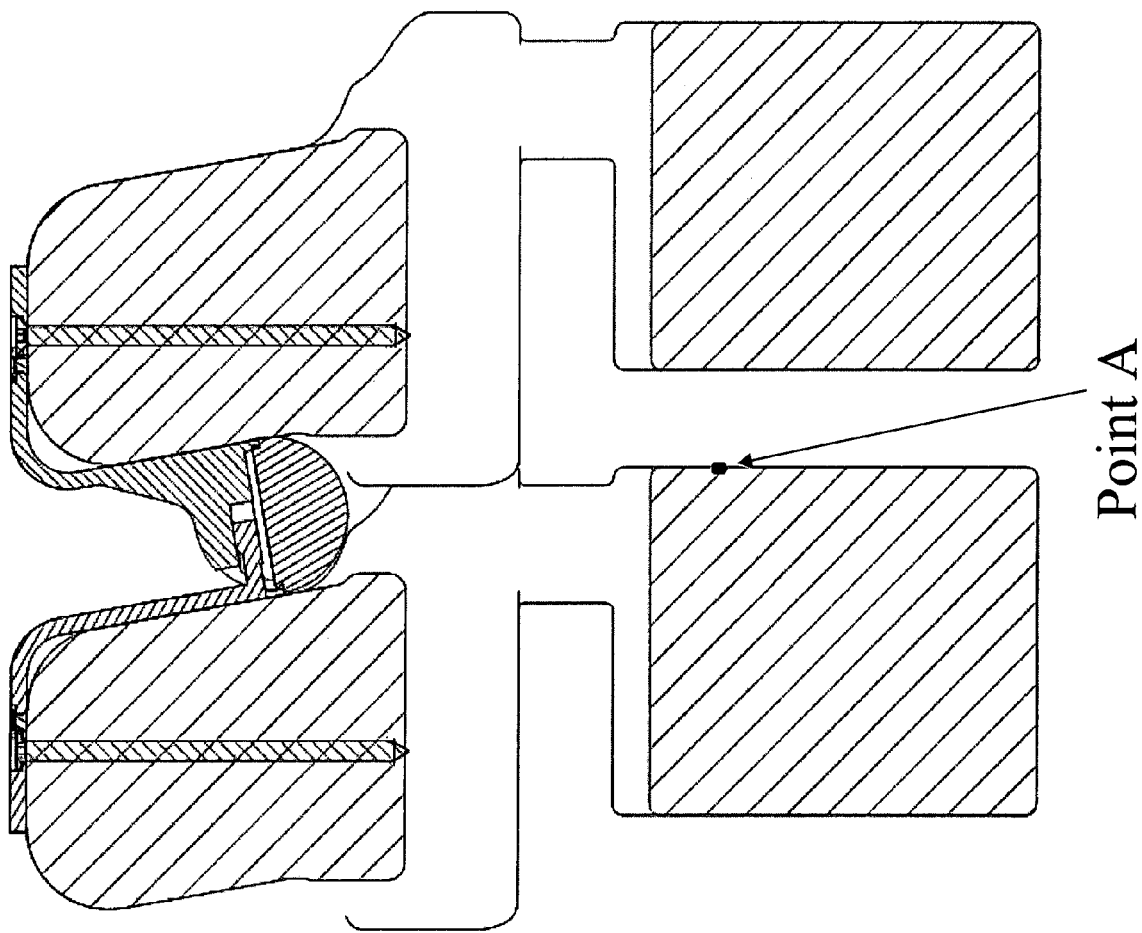
FIG. 20 shows a side, cross-sectional view of the device mounted to a pair of vertebrae.

FIG. 20 shows a side, cross-sectional views of the device mounted to a pair of vertebrae. The members 115 can be coupled to one another by mating the member 425 beneath the member 430 such that articulating surfaces abut one another and permit rotational movement therebetween. The member 440 is positioned below the member 430 and secured thereto such as in a threaded relationship. This retains the device in the assembled state.

Figure 21:
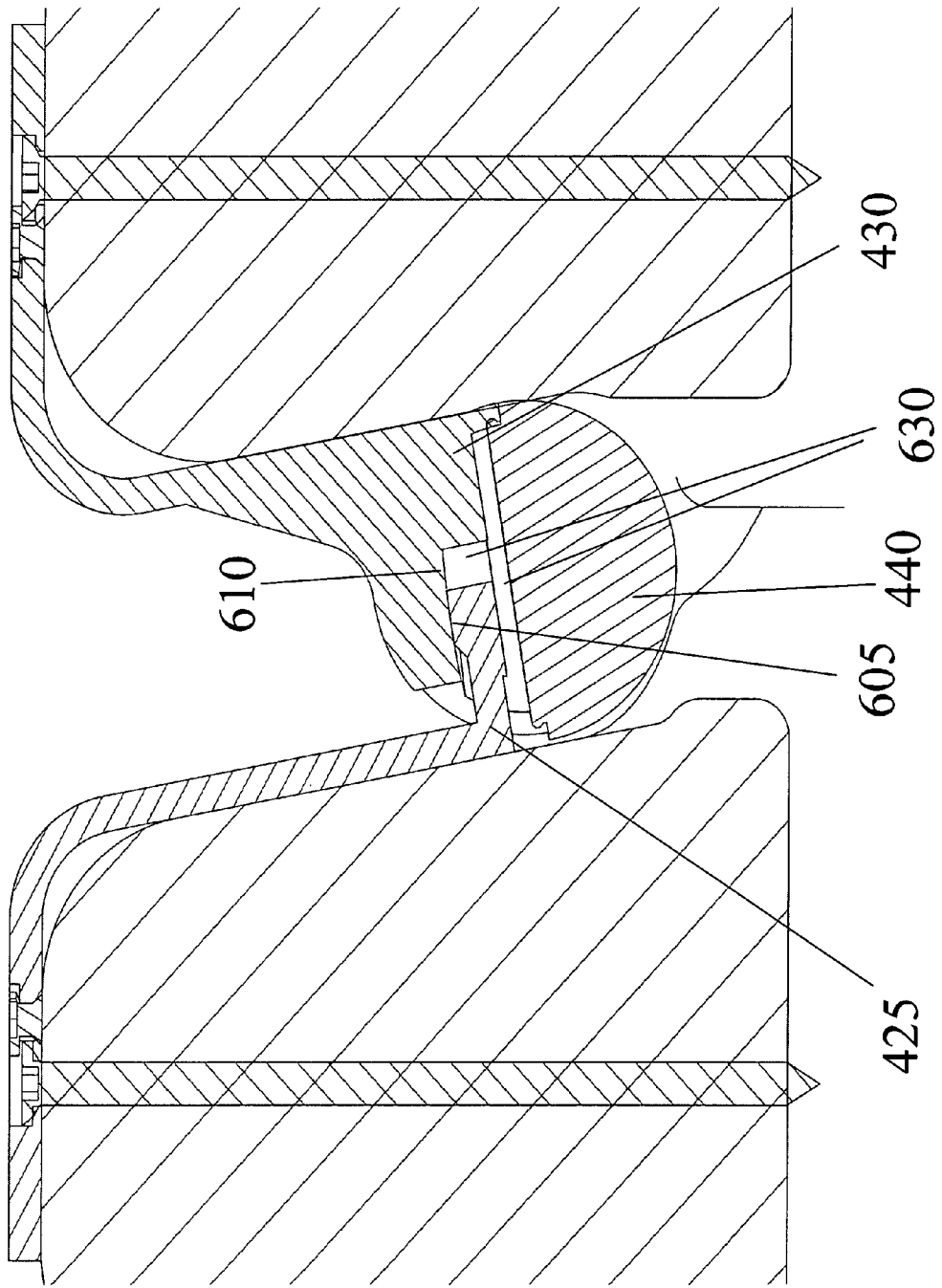
FIG. 21 shows a side, cross-sectional view of the device mounted to a pair of vertebrae.

FIG. 21 shows an enlarged, cross-sectional view of the device in the assembled state and mounted between vertebrae. The member 425 has a rounded surface 605. The surface 605 interacts with a complimentary rounded surface 610 on the member 430. A space 630 is formed when the member 440 is secured onto the member 430. The member 425 resides within the space 630 in the assembled device. The space 630 permits a certain amount of "play" between the articulation of members 430 and 425. In an embodiment, the space 630 contains a malleable member that keeps members 425 and 430 in a preferred, neutral position and acts to return these members to the neutral position when they move away from it.

In addition, the curvilinear surfaces 605 and 610 define a spherical path of motion that is centered at Point A (shown in FIG. 20). That is, the surfaces 605 and 610 can move relative to one another along a pathway that is curvilinear or spherical. Alternative motion paths that are non-spherical may be alternatively made. In specific, a configuration that is similar, but not identical, to a hyperbolic paraboloid may be incorporated within the articulating surface. Moreover, the interaction of the protrusion 445 and indentation 450 allows a variable degree of rotational movements of one vertebral body relative to the other. The extent of rotation and lateral flexion permitted is dependent on the degree of flexion of the vertebral bodies. That is, with the vertebral bodies in flexion, the extent of rotation and lateral flexion permitted by the device is greater that amount of rotation and lateral flexion that is permitted when the vertebral bodies are in extension. This feature reproduces the natural motion characteristics between the vertebral bodies.

Figure 22:
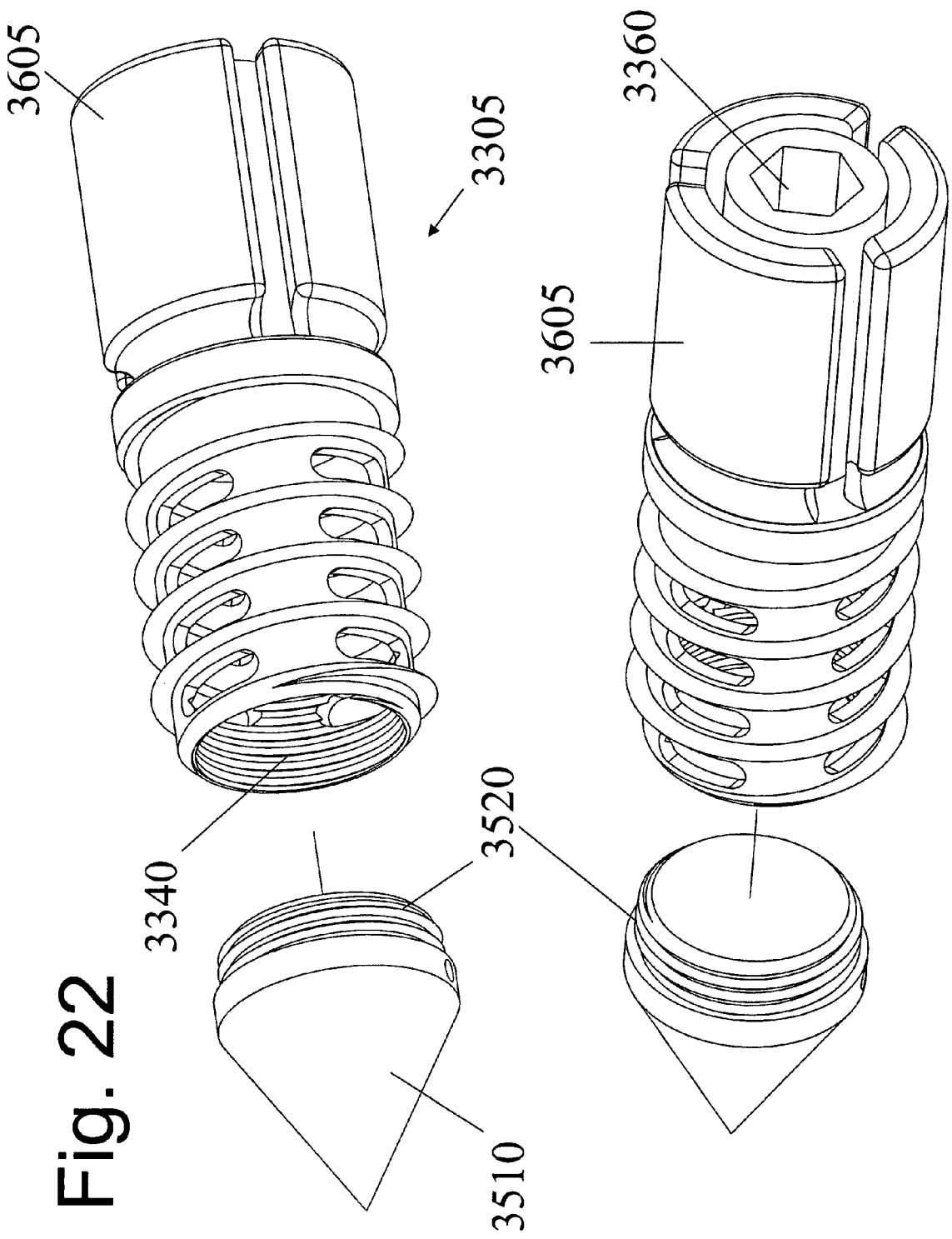
FIG. 22 shows perspective views of another embodiment in the disassembled state.
Figure 23:
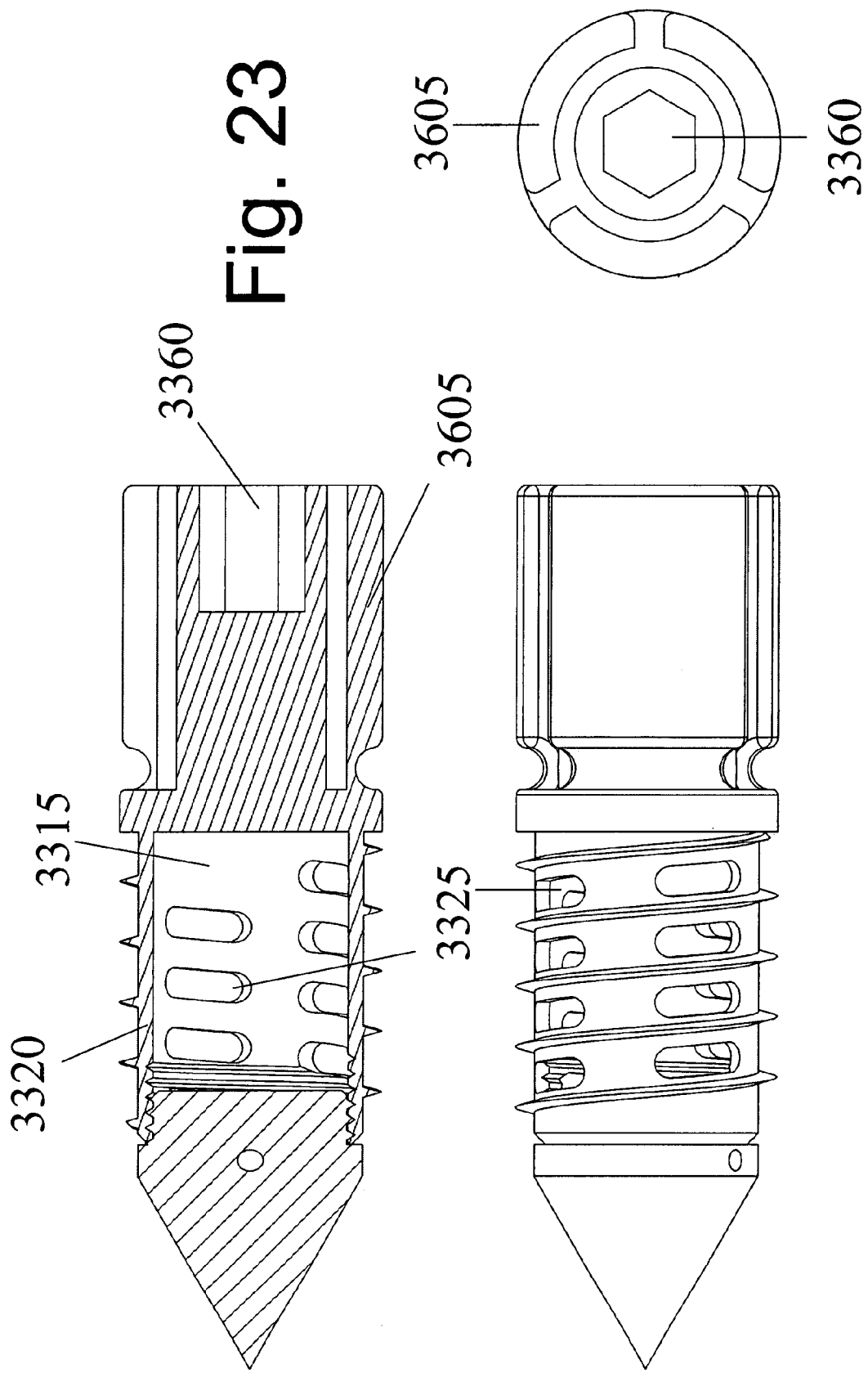
FIG. 23 shows additional views of the assembled implant of FIG. 22.

FIG. 22 illustrates perspective views of device 3305 in the disassembled state. FIG. 23 shows sectional views of the assembled device 3305. Threaded wall 3320 surrounds central cavity 3315 and contains multiple full thickness bore holes 3325. The distal aspect of wall 3320 contains interior threads 3340 that couple with complimentary threads 3520 of distal member 3510. The central cavity 3315 is adapted to house a bone graft or bone graft substitute and permit fusion between the bone graft within cavity 3315 and the vertebral bone surrounding the outer aspect of device 3305. After placement of bone graft material within cavity 3315, distal member 3510 is screwed onto device 3305. The fusion forms across bore holes 3325.

The proximal aspect of device 3305 contains hexagonal cut out 3360. Cut out 3360 is adapted to accept a hex screw driver and the latter is used to drive device 3305 into bone. The proximal aspect of device 3305 contains at least one flap 3605 that is movably attached to device 3305. When a force is applied to the proximal aspect of device 3305, flap 3605 transiently and reversibly moves towards the center line of the device. In this way, flap 3605 functions as a malleable member and imparts a spring-like quality to the proximal aspect of device 3305.

Figure 24:
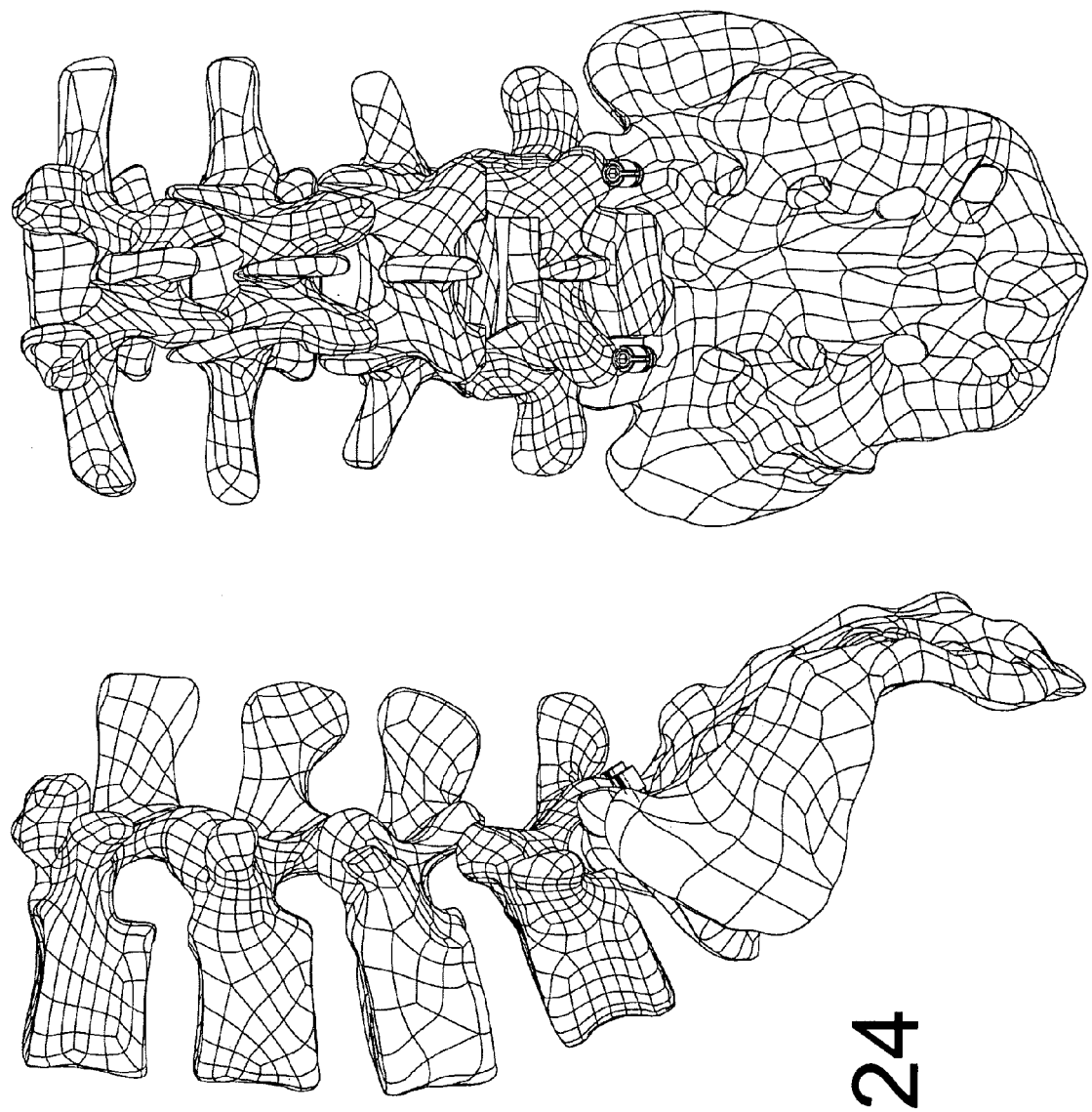
FIG. 24 shows the implant of FIG. 22 mounted on the sacrum.
Figure 25:
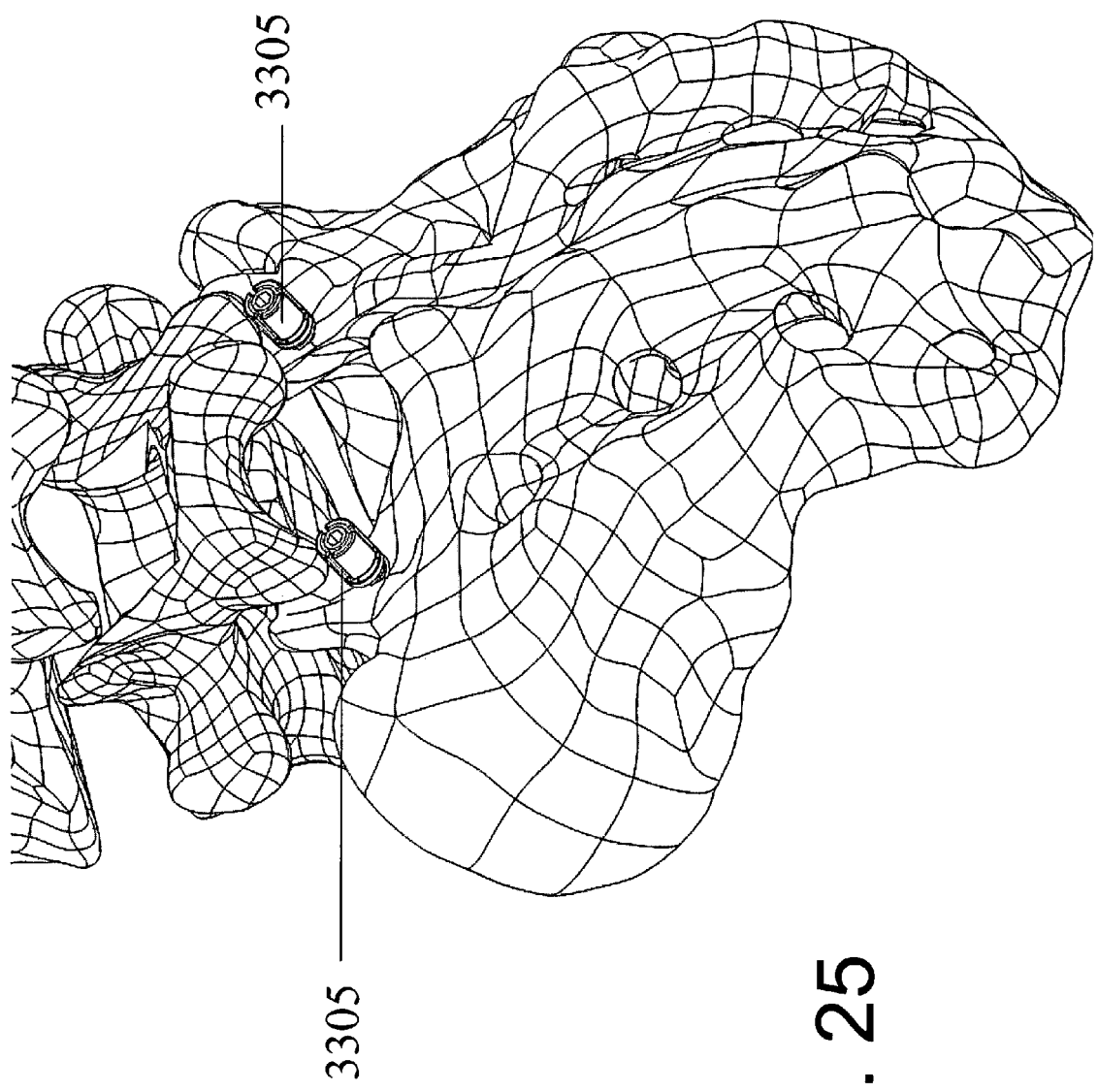
FIG. 25 illustrates an oblique view of the mounted implant of FIG. 24.

In use, the central cavity 3315 is filed with a bone graft and distal member 3510 is threaded onto device 3305. Once assembled, distal member 3510 is rigidly attached to 3305. Under x-ray guidance, the device is percutaneously driven into the base of the superior articulating surface of the lower vertebral body and abuts the inferior surface of the inferior articulating surface of the superior vertebra. Preferably, a single device is used on each side of the vertebral midline, so that two devices 3305 are used at each stenotic level. The devices are shown attached to bone in FIGS. 24 and 25. As illustrated, each device 3305 limits the downward travel of the inferior articulating surface of the superior vertebra and limits the degree of extension at that spinal level. With time, the bone contained within cavity 3315 will fuse with the adjacent bone and rigidly anchor the device to the vertebra. Because of the fusion, the device does not to be anchored into the pedicle portion of the vertebra and it can be short in length.

Figure 26:
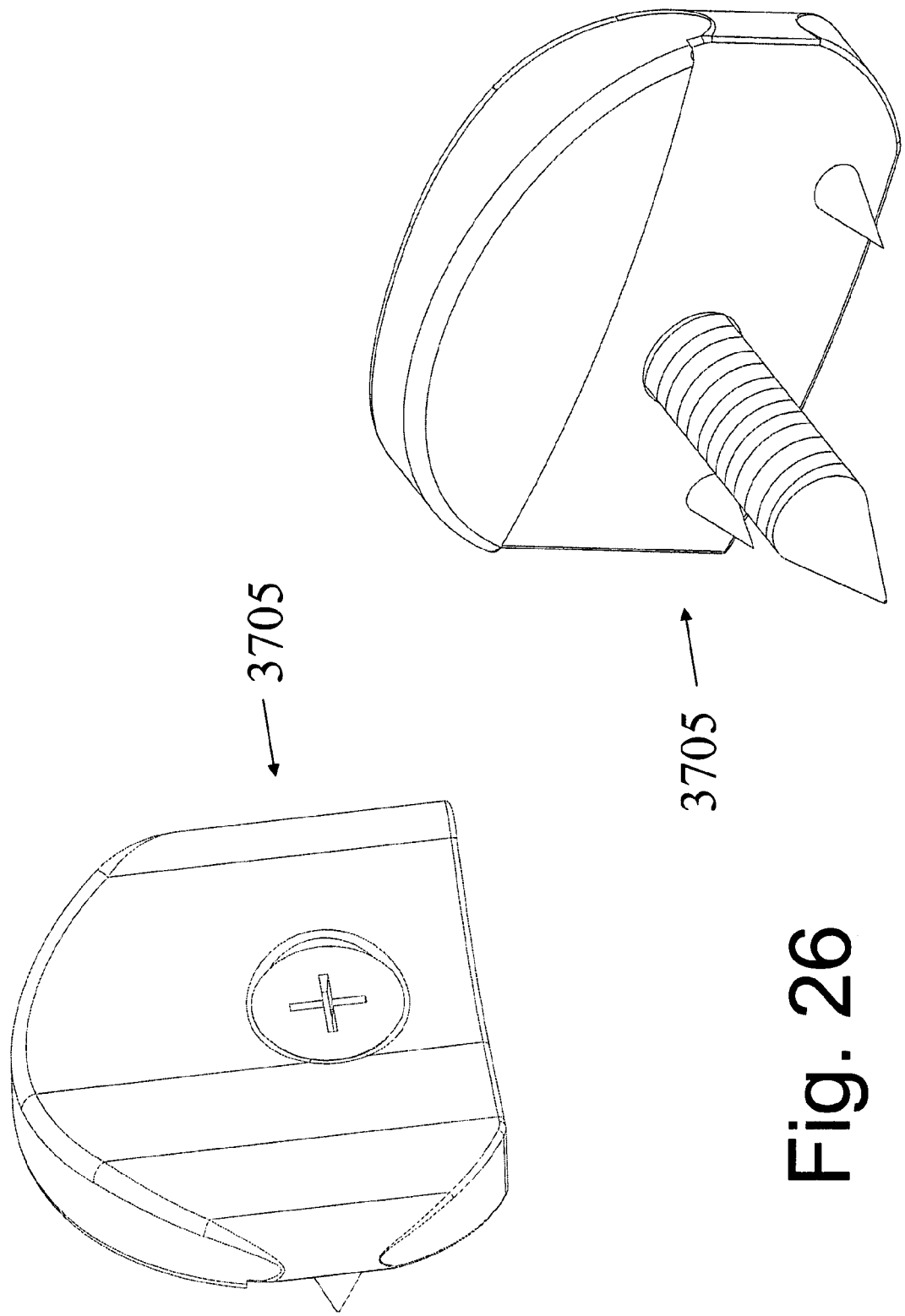
FIG. 26 shows an additional embodiment.

FIG. 26 illustrates device 3705. The device is intended to reside within the facet joint and be anchored onto one, but not both, of the adjacent vertebras. The device may be affixed onto the vertebral bone using pins and a bone screw or the device may be at least partially comprised of a bone graft or bone graft substitute so as to fuse onto the adjacent bone. The device may be coated/made with osteo-conductive (such as demineriized bone matrix, hydroxyapatite, and the like) and/ or osteo-inductive (such as Transforming Growth Factor "TGF-B," Platelet-Derived Growth Factor "PDGF," Bone-Morphogenic Protein "BMP," and the like) bio-active materials that promote bone formation. Further, one or more surfaces may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant.

Figure 27B:
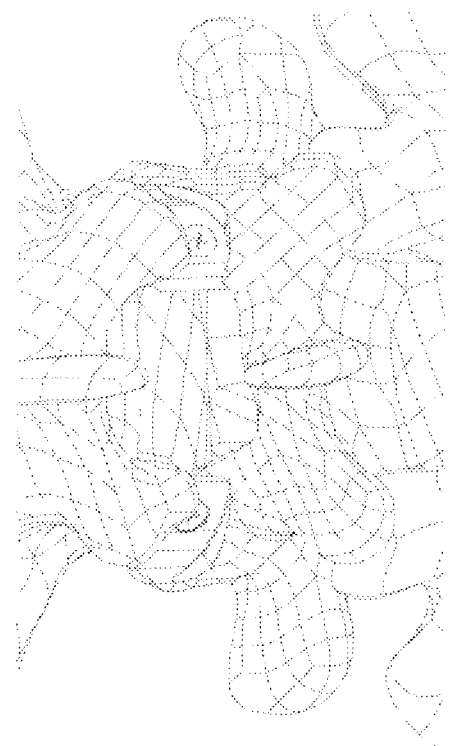
FIGS. 27A and B show the implant of FIG. 26 placed into the spinal column.
Figure 27A:
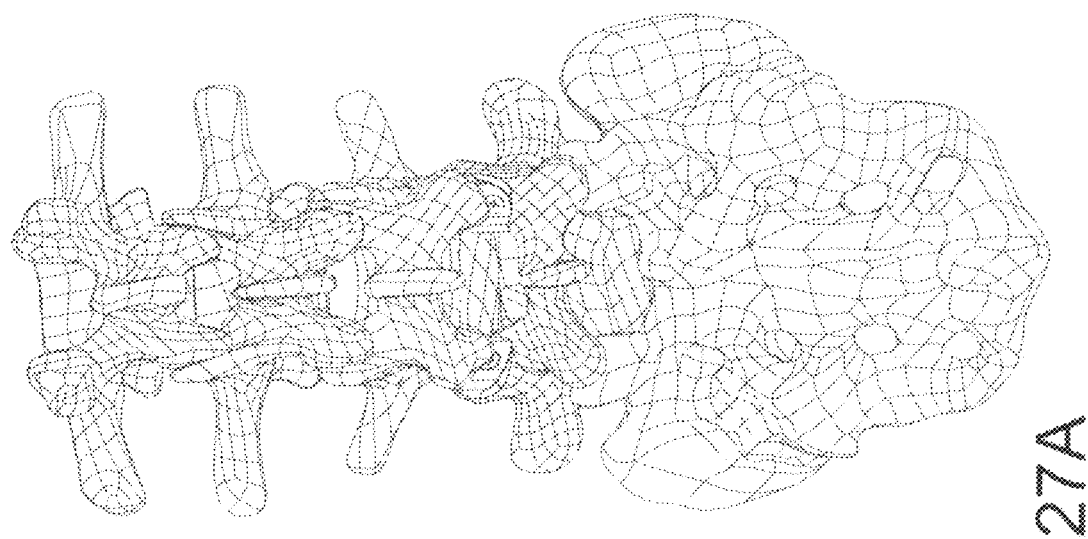

The device is shown anchored to bone in FIGS. 27A and 27B. It is intended to at least partially replace the function of a natural facet joint that been at least partially removed at surgery. It may alternatively be used within an intact but degenerated facet joint to reestablish a functional articulation.

Figure 28A:
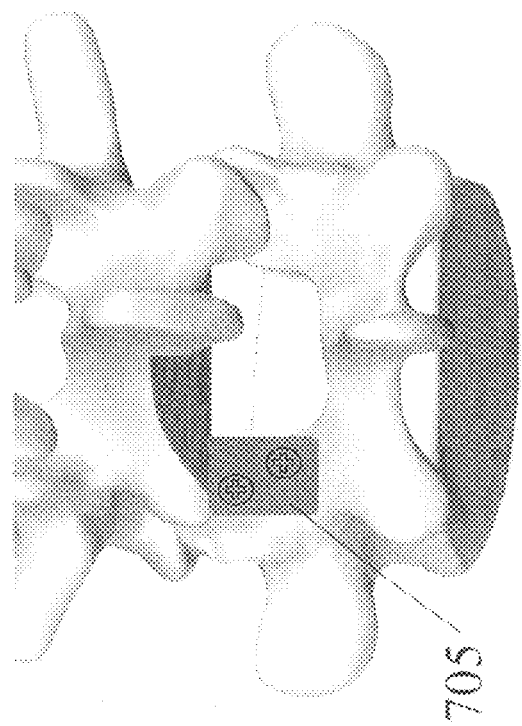
FIG. 28A shows an additional embodiment of an orthopedic implant.

FIG. 28A shows an additional embodiment of an orthopedic implant 705 positioned on two vertebral bodies of the lumbar spine. The implant 705 is attached onto the superior articulating surface and lamina of the lower vertebra and functions to stop the downward movement of the inferior articulating surface of the upper vertebral body. In this way, the device stops the extension of the two vertebral bodies and keeps them in relative flexion. The device can include contains one or more bore holes through which one or more screws are passed and anchored onto the underlying bone. As shown, the inferior aspect of the lamia of the upper vertebra is preferably removed (laminotomy) to decompress the nerve elements prior to device placement.

Figure 28B:
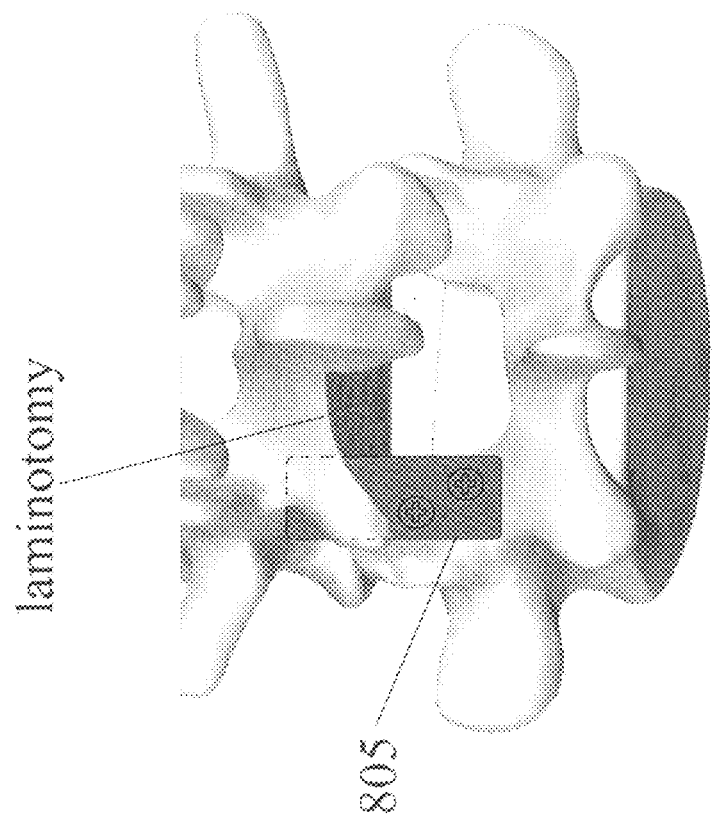
FIG. 28B shows an additional embodiment of an orthopedic implant.
Figure 29B:
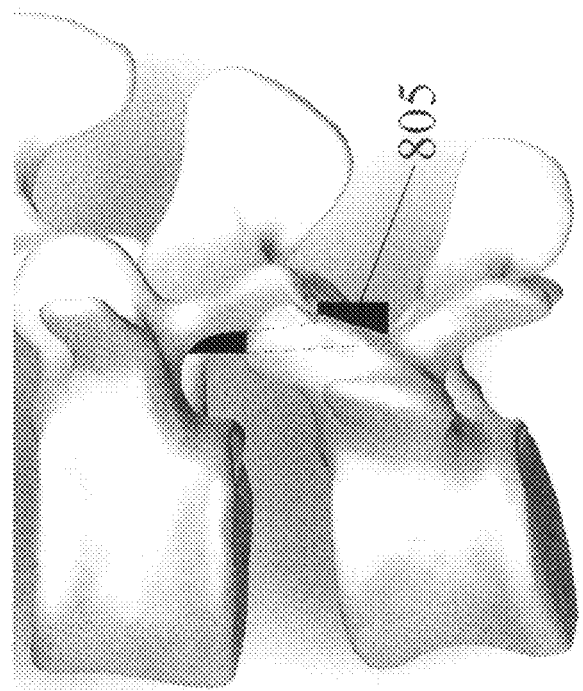
FIG. 29B shows the implant in place.
Figure 29A:

FIG. 28B shows an additional embodiment of an orthopedic implant 805 positioned on two vertebral bodies of the lumbar spine. The implant 805 is attached onto the superior articulating surface and lamina of the lower vertebra and transverses the facet joint between the two vertebral bodies. The superior surface of the device abuts the inferior aspect of the pedicle of the upper vertebral body. The implant functions to stop the extension of the two vertebral bodies and keeps them in relative flexion. The implant 805 can contain one or more bore holes through which screws are passed and anchored onto the underlying bone. FIG. 29A shows a lateral view of the vertebral bodies and FIG. 29B shows the implant 805 in place. Note that implant placement will necessarily place the lower articulating surface of the upper vertebral body more posteriorly and at least partially realign an anterior spondylolisthesis.

Figure 30A:
FIGS. 30A and 30B show an additional embodiment of an implant.
Figure 30B:
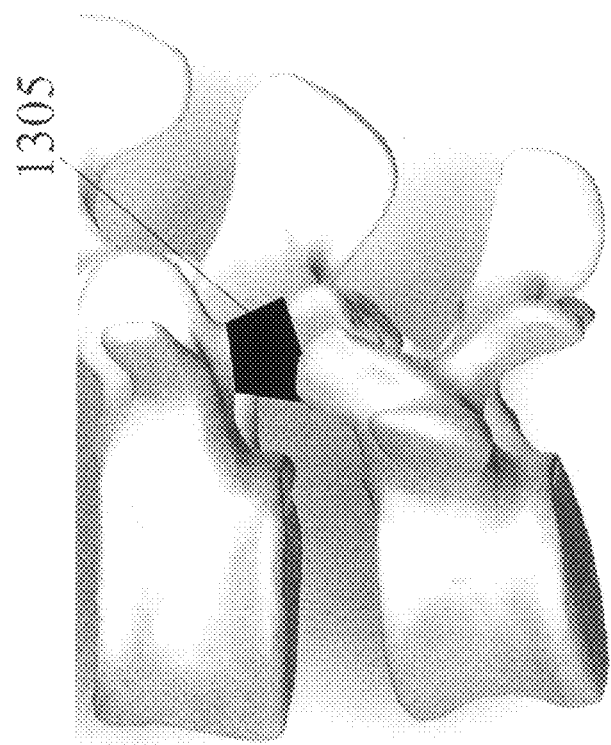
Figure 31:
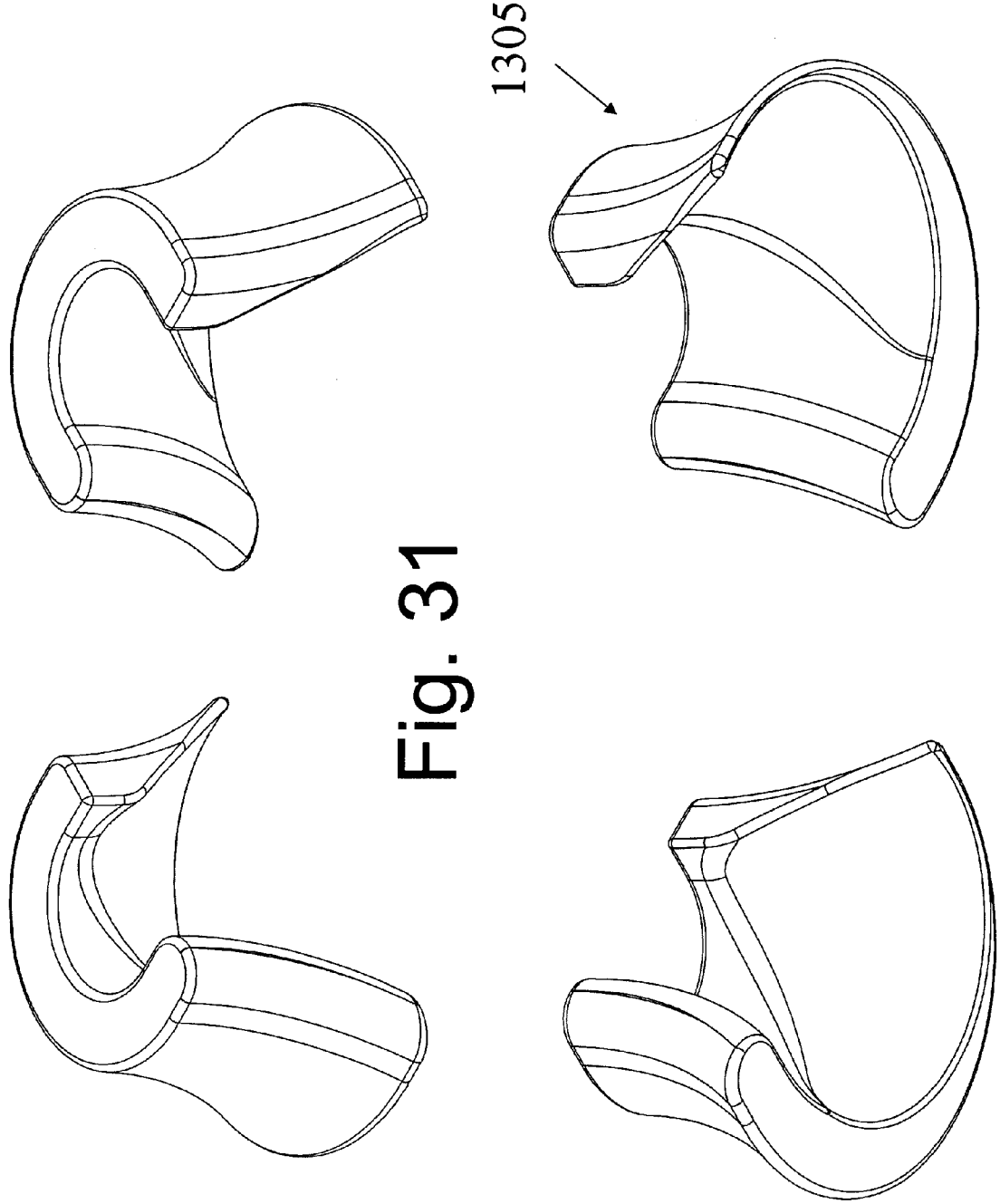
FIG. 31 shows perspective views of the implant.

FIGS. 30A and 30B show an additional embodiment of an implant 1305. In an embodiment, the implant 1305 is a "C" shaped implant. FIG. 31 shows perspective views of the implant 1305. The implant 1305 functions to separate the top of the superior articular surface of the inferior body from the inferior aspect of the pedicle of the upper vertebral body. The implant 1305 has a size and shape such that the opening of the "C" can be positioned over at least a portion of the vertebral body. In an embodiment, a separate attachment device is not used to attach the implant 1305 to bone. In another embodiment, the implant 1305 contain one or more bore holes through which screws are passed and anchored onto the underlying bone. FIG. 32 shows the implant 1305 positioned on the bone.

The disclosed devices or any of their components can be made of any biologically adaptable or compatible materials. Materials considered acceptable for biological implantation are well known and include, but are not limited to, stainless steel, titanium, tantalum, combination metallic alloys, various plastics, resins, ceramics, biologically absorbable materials and the like. Any components may be also coated/made with osteo-conductive (such as demineriized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. Lastly, the system or any of its components can also be entirely or partially made of a shape memory material or other deformable material.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A method for placement of an orthopedic implant within a target inter-spinous space of a spinal column, comprising:
   visualizing the target inter-spinous space using an imaging modality;
   advancing at least a first extension member and a second extension member of an implant placement device towards the inter-spinous space, wherein each of the first extension member
   and the second extension member has an elongated segment that extends from a proximal aspect to a distal aspect, wherein the proximal aspect of each of the first and second extension members is connected to a distraction mechanism of the implant placement device and wherein the distraction mechanism is adapted to forcibly move the first extension member relative to the second extension member, and wherein a bore extends from a proximal opening to distal opening in between the first and second extension members and forms a guide channel for the advancement of the orthopedic implant;

positioning at least a portion of the distal segment of each of the first and second extension members within the target inter-spinous space;

actuating the distraction mechanism of the implant placement device and moving the first and second extension members away from one another, wherein actuation of the distraction mechanism produces at least some expansion of the target inter-spinous space;

advancing the orthopedic implant at least partially through the guide channel that is in between the first and second extension members until at least a portion of the implant is positioned within the target inter-spinous space, wherein at least a first segment of the implant is positioned within the guide channel and at least a second segment of the implant is positioned outside of the guide channel during the implant's advancement within the target inter-spinous space;

removing the extension members of the implant placement device from the inter-spinous space, wherein after extension member removal the orthopedic implant remains positioned within the inter-spinous space and maintains the spinous process of the first and second vertebral bones separated by a desired distance.

2. A method as in claim 1, wherein a surface of the first extension member forms at least a segment of the guide channel that is used for orthopedic implant placement.

3. A method as in claim 1, wherein a surface of the second extension member forms at least a segment of the guide channel that is used for orthopedic implant placement.

4. A method as in claim 1, wherein the first extension member extends away from the distraction mechanism along a first trajectory and wherein at least a segment of the first trajectory is curvilinear.

5. A method as in claim 1, wherein the second extension member extends away from the distraction mechanism along a second trajectory and wherein at least a segment of the second trajectory is curvilinear.

6. A method as in claim 1, wherein the guide channel extends from a proximal end to a distal end along a trajectory, and wherein at least a segment of the trajectory is curvilinear.

7. A method as in claim 1, wherein an elongated member is slidably positioned within the guide channel during advancement of the first and second extension members towards the inter-spinous space, wherein a distal end of the elongated member extends beyond the distal end of the guide channel, and wherein the distal end of elongated member is shaped to separate tissues ahead of the advancing extension members.

8. A method as in claim 1, wherein the elongated member is removed from in between the first and second extension members prior to advancement of the orthopedic implant through the guide channel.

9. A method as in claim 1, wherein the method is performed in a minimally invasive manner.

10. A method as in claim 1, wherein the method is performed in a percutaneous manner.

11. A method as in claim 1, wherein a region of the implant placement device provides an indicia of the distance between the first and second extension members.

12. A method as in claim 1, wherein a region of the implant placement device provides an indicia of a size of the orthopedic implant appropriate for placement into the target inter-spinous space.

13. A method as in claim 1, wherein a region of the implant placement device provides an indicia of a value of the distraction force delivered to the first and second extension members by the distraction mechanism.

14. A method as in claim 1, wherein the orthopedic implant is comprised of at least two segments that are movable relative to one another.

15. A method as in claim 1, wherein the orthopedic implant is adapted to transition from a first size to a second size after advancement into the target inter-spinous space.

16. A method as in claim 15, wherein the second size is greater than the first implant size.

17. A method for placement of an orthopedic implant within a target inter-spinous space of a spinal column comprising:

visualizing the target inter-spinous space using an imaging modality;

advancing a distal aspect of an orthopedic implant insertion assembly towards the target inter-spinous space, wherein the assembly comprises:

a first extension member and a second extension member each having at least an elongated segment, wherein each elongated segment extends from a proximal aspect to a distal aspect along a curvilinear trajectory, wherein the elongated segments of the first and second extension members are oppositely aligned with at least the proximal aspect and distal aspect of each extension member positioned in proximity, and wherein a bore extends a first distance from a proximal opening to a distal opening, wherein the elongated bore is positioned in between the first and second extension members, and wherein at least a segment of the bore forms a curvilinear guide channel for the advancement of the orthopedic implant; and an elongated member that is slidably positioned within the curvilinear guide channel, wherein the elongated member extends from a proximal end to a distal end for a distance greater than the first distance of the guide channel, wherein the distal end of the elongated member is shaped to separate tissues ahead of the advancing extension members and wherein the elongated member, when positioned within the guide channel, prevents advancement of the orthopedic implant through the guide channel;

positioning the distal aspect of the implant insertion device in proximity to the inter-spinous space;

advancing the orthopedic implant through the curvilinear guide channel and guiding at least a portion of the implant into the target inter-spinous space, wherein at least a first segment of the implant is positioned within the guide channel and at least a second segment of the implant is positioned outside of the guide channel during the implant's advancement within the target inter-spinous space.

18. A method as in claim 17, wherein the orthopedic implant insertion device further comprises a third member that is coupled to a proximal segment of each of the first and second extension members, wherein the third member comprises an actuatable mechanism that is adapted to reversibly change the distance between the first and second extension member and wherein actuation of the actuatable mechanism changes a size of the guide channel.

19. A method as in claim 18, wherein actuation of the actuatable mechanism produces at least some movement of the spinous process of the first vertebral bone relative to the spinous process of the second vertebral bone.

20. A method as in claim 18, wherein a region of the implant placement device provides an indicia of a value of the distraction force delivered to the first and second extension members by the actuatable mechanism.

21. A method as in claim 17, wherein a region of the implant insertion device provides an indicia of the distance between the first and second extension members.

22. A method as in claim 17, wherein a region of the implant insertion device provides an indicia of a size of the implant appropriate for placement into the target inter-spinous space.

23. A method as in claim 17, wherein a surface of the first extension member forms at least a segment of the guide channel that is used for implant placement.

24. A method as in claim 17, wherein a surface of the second extension member forms at least a segment of the guide channel that is used for implant placement.

25. A method as in claim 17, wherein the method is performed in a minimally invasive manner.

26. A method as in claim 17, wherein the method is performed in a percutaneous manner.

27. A method as in claim 17, wherein the orthopedic implant is comprised of at least two segments that are movable relative to one another.

28. A method as in claim 17, wherein the orthopedic implant is adapted to transition from a first size to a second size after advancement into the target inter-spinous space.

29. A method as in claim 28, wherein the second implant size is greater than the first size.

* * * * *